United States Patent [19]

Sawaki et al.

[11] 3,989,504
[45] Nov. 2, 1976

[54] HERBICIDAL COMPOSITION OF 3,4-DIHYDRO-2H-PYRANE-2,4-DIONES AND METHODS

[75] Inventors: Mikio Sawaki; Isao Iwataki, both of Odawara; Yoshihiko Hirono, Hiratsuka; Hisao Ishikawa, Oiso; Shozo Yamada, Hiratsuka; Yasushi Yasuda, Hiratsuka; Mitsuo Asada, Hiratsuka, all of Japan

[73] Assignee: Nippon Soda Company Limited, Tokyo, Japan

[22] Filed: July 3, 1975

[21] Appl. No.: 592,911

Related U.S. Application Data

[62] Division of Ser. No. 406,621, Oct. 15, 1973, Pat. No. 3,927,034.

[30] Foreign Application Priority Data

Oct. 20, 1972 Japan............................. 47-104962
Dec. 25, 1972 Japan.................................. 48-2526
Dec. 25, 1972 Japan.................................. 48-2527

[52] U.S. Cl. .................................................. 71/88
[51] Int. Cl.² ............................................ A01N 9/00
[58] Field of Search .......................................... 71/88

[56] References Cited
UNITED STATES PATENTS 3,927,034   12/1975   Sawaki et al..................... 260/343.5

FOREIGN PATENTS OR APPLICATIONS 46-16916   5/1971   Japan........................................ 71/88

*Primary Examiner*—Joseph Paul Brust
*Attorney, Agent, or Firm*—George B. Oujevolk

[57] ABSTRACT

A compound of the formula

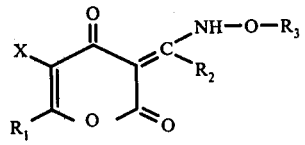

wherein X is hydrogen or halogen:
  $R_1$ is alkyl having six or less carbon atoms or phenyl;
  $R_2$ is alkyl having 1 to 20 carbon atoms or haloalkyl having six or less carbon atoms or phenyl or phenyl substituted with halogene or nitro or benzyl or phenoxymethyl or 2-phenylvinyl;
  $R_3$ is hydrogen or alkyl having 1 to 10 carbon atoms or alkenyl having six or less carbon atoms or alkynyl having six or less carbon atoms or benzyl; a proviso that $R_1$ and $R_2$ do not simultaneously represent a methyl group, is useful as herbicide.

18 Claims, 30 Drawing Figures

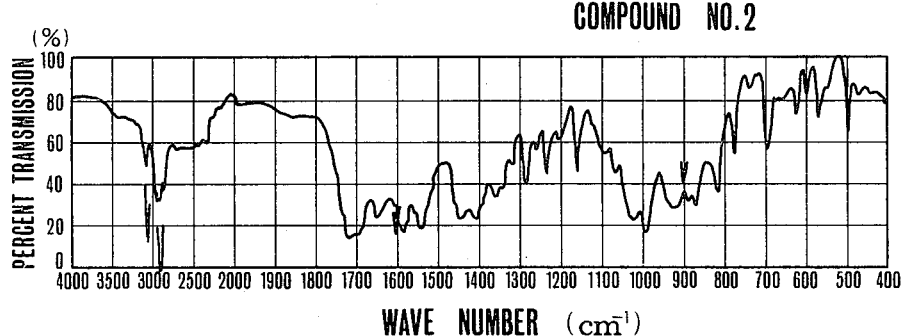
FIG. 1 COMPOUND NO. 2
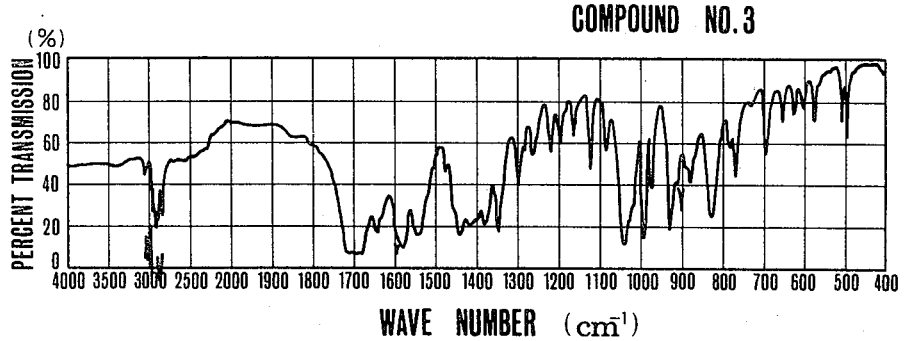
FIG. 2 COMPOUND NO. 3
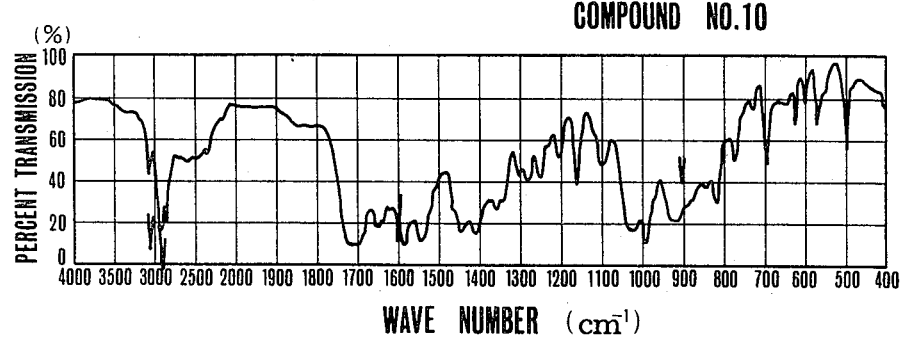
FIG. 3 COMPOUND NO. 10

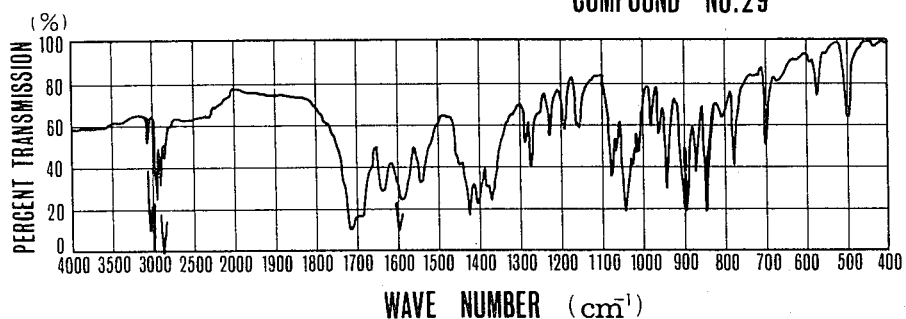
FIG. 4 — COMPOUND NO. 29
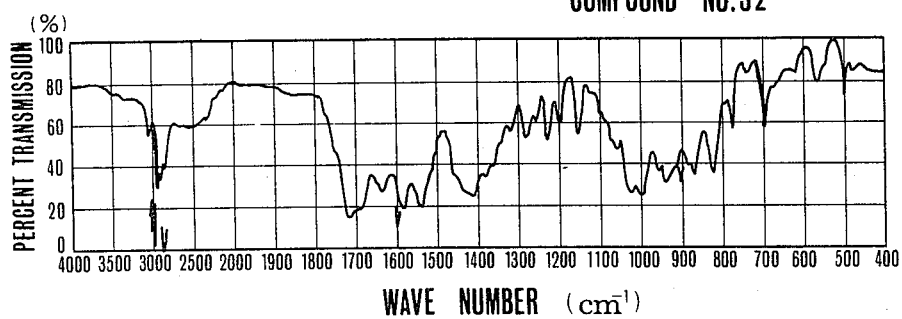
FIG. 5 — COMPOUND NO. 32
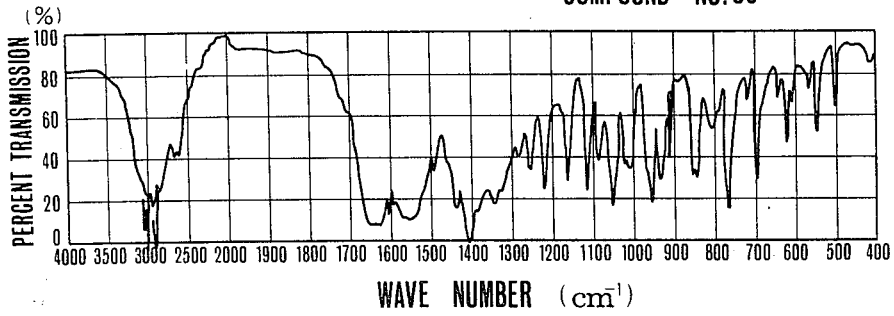
FIG. 6 — COMPOUND NO. 39

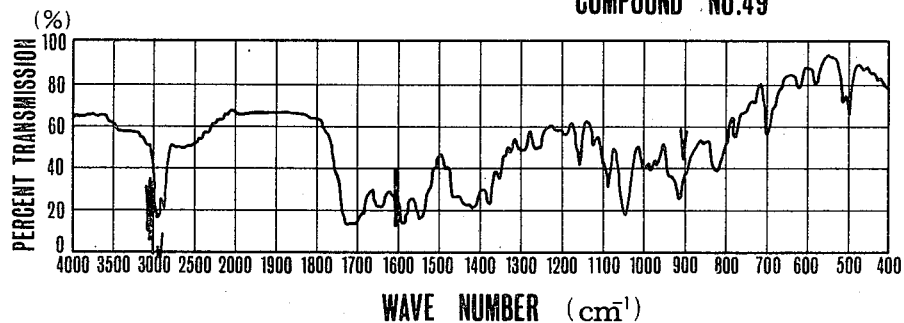
FIG. 7 — COMPOUND NO. 49
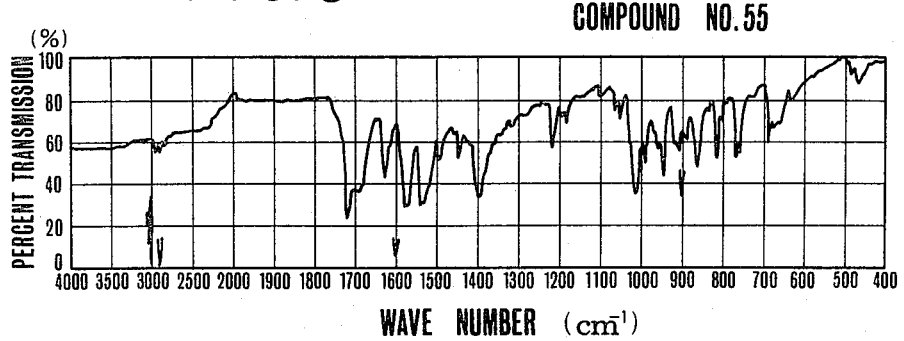
FIG. 8 — COMPOUND NO. 55
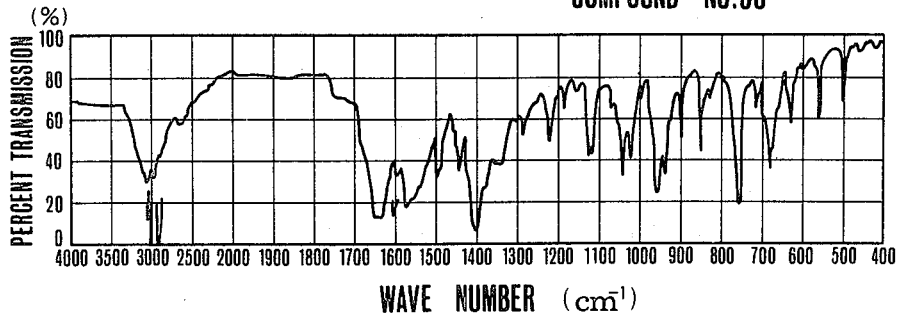
FIG. 9 — COMPOUND NO. 58

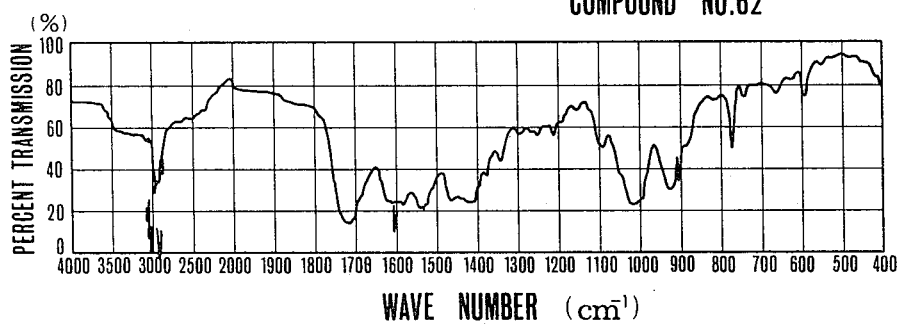
FIG.10 — COMPOUND NO.62
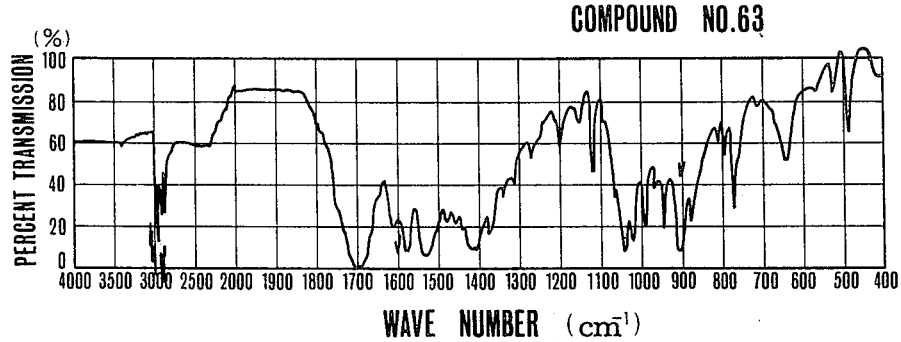
FIG.11 — COMPOUND NO.63
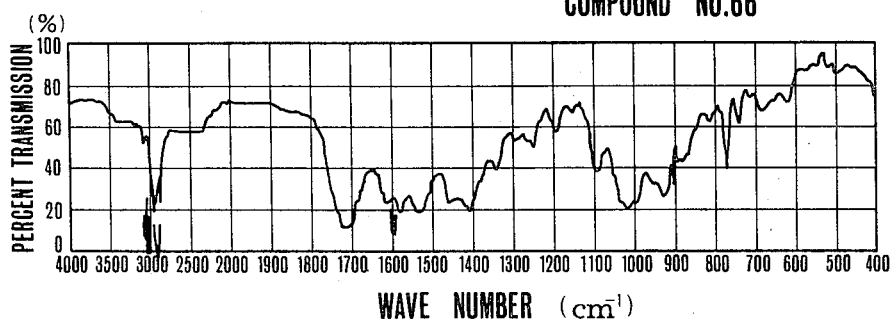
FIG.12 — COMPOUND NO.66

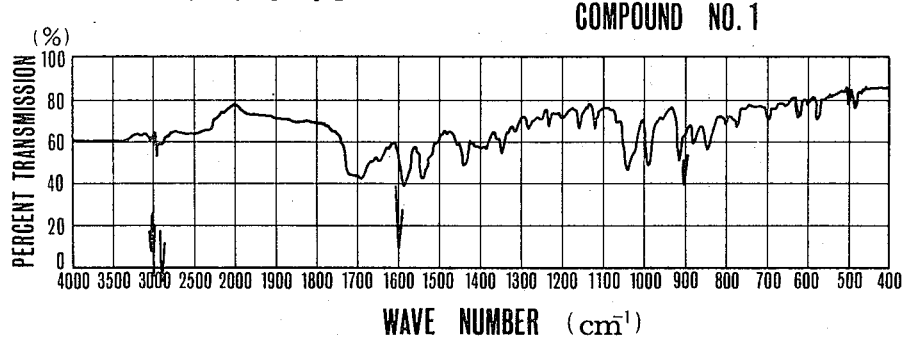
FIG. 13 COMPOUND NO. 1
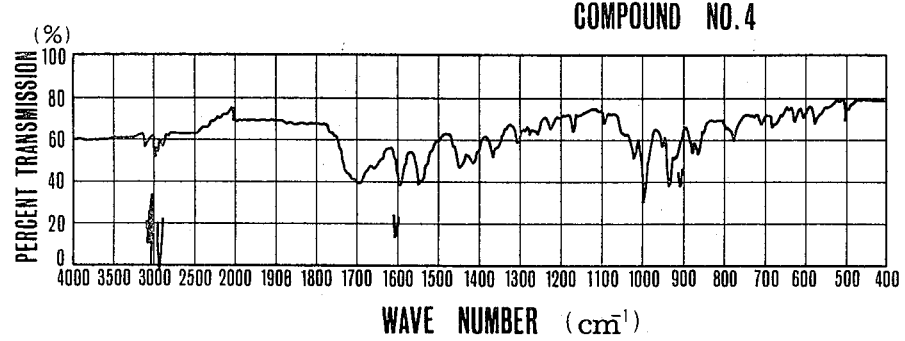
FIG. 14 COMPOUND NO. 4
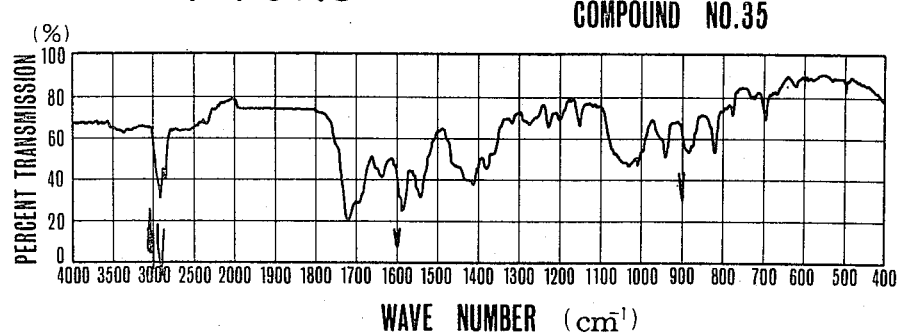
FIG. 15 COMPOUND NO. 35

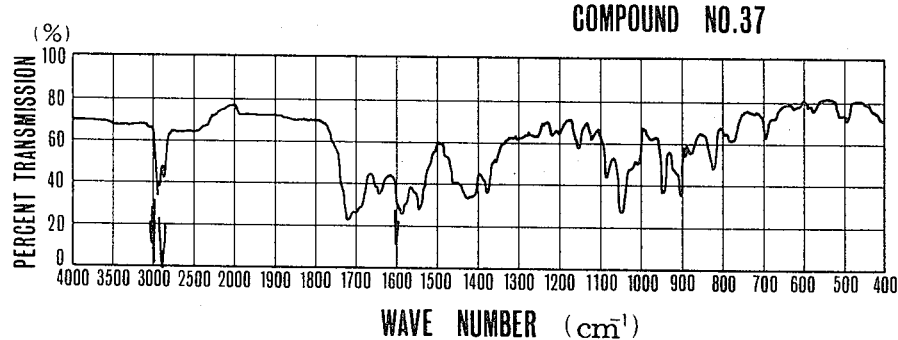
FIG.16 — COMPOUND NO.37
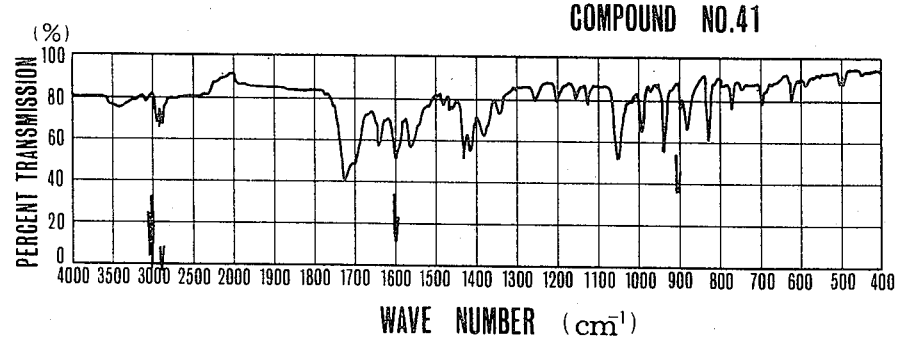
FIG.17 — COMPOUND NO.41
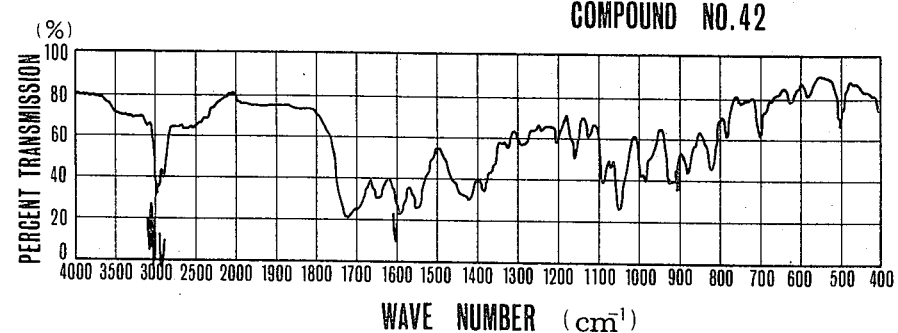
FIG.18 — COMPOUND NO.42

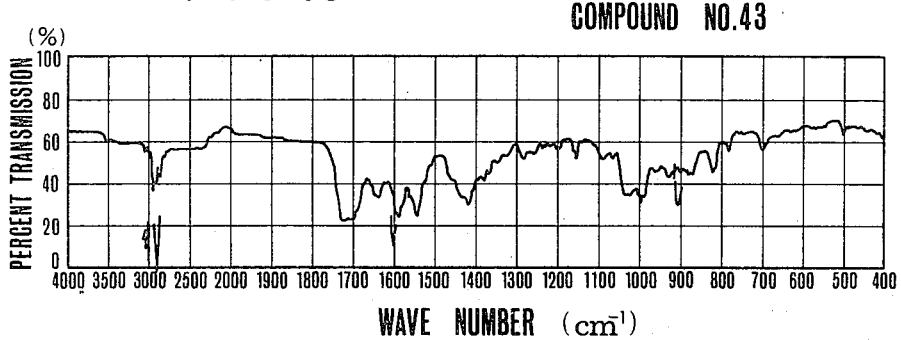
FIG.19 COMPOUND NO.43
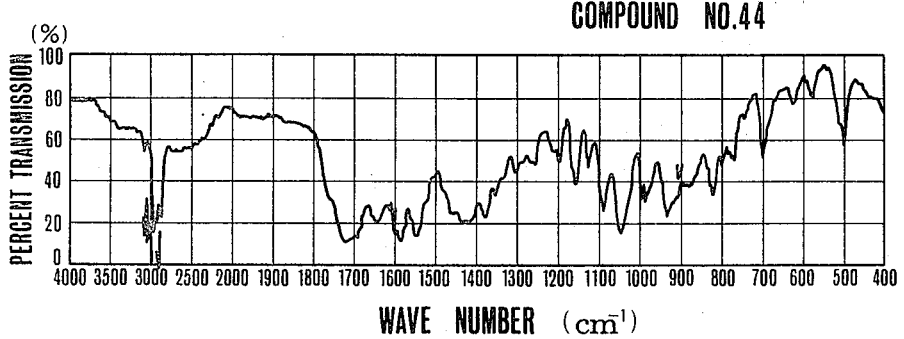
FIG.20 COMPOUND NO.44
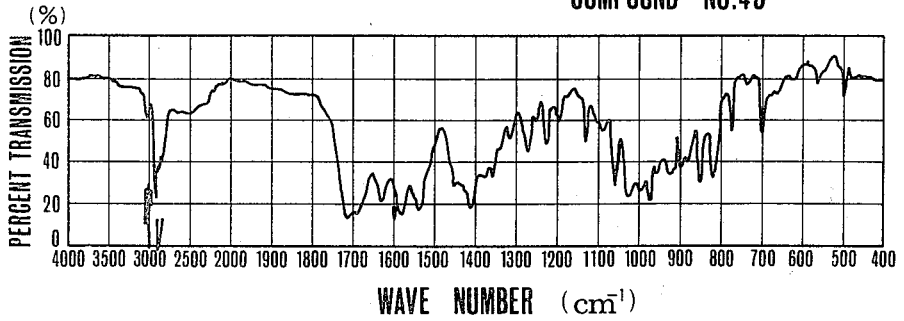
FIG.21 COMPOUND NO.45

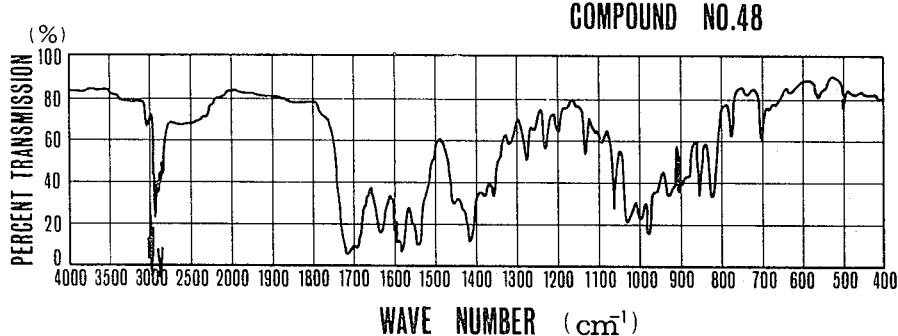
FIG.22 COMPOUND NO.48
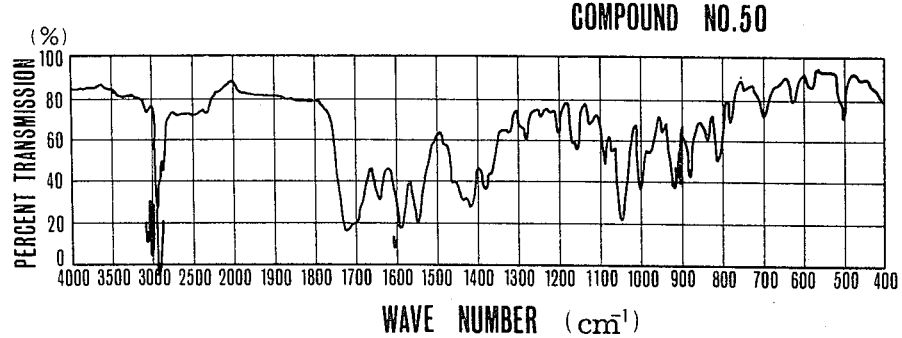
FIG.23 COMPOUND NO.50
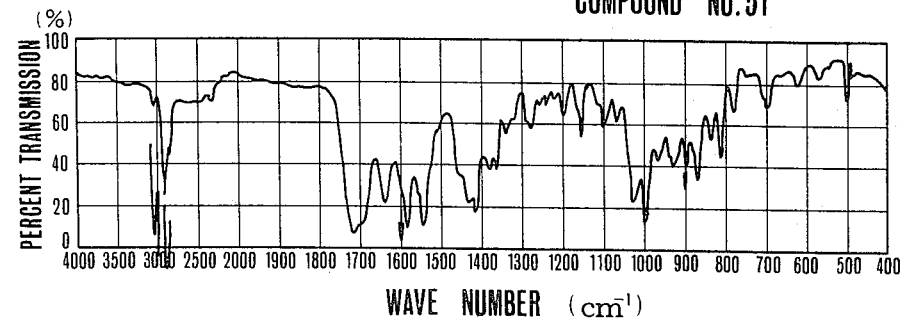
FIG.24 COMPOUND NO.51

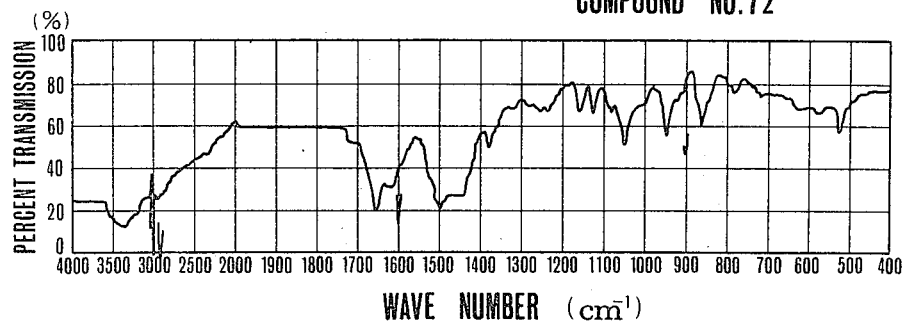
FIG.25 COMPOUND NO.72
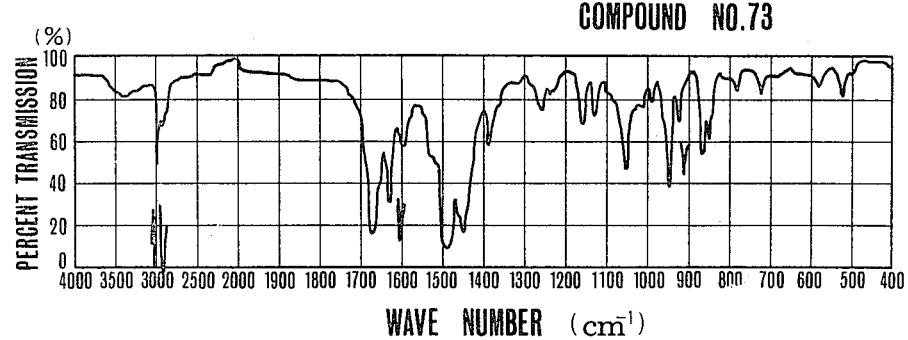
FIG.26 COMPOUND NO.73
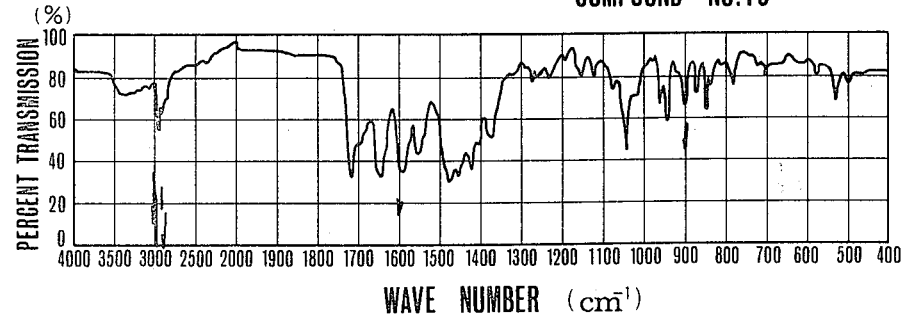
FIG.27 COMPOUND NO.75

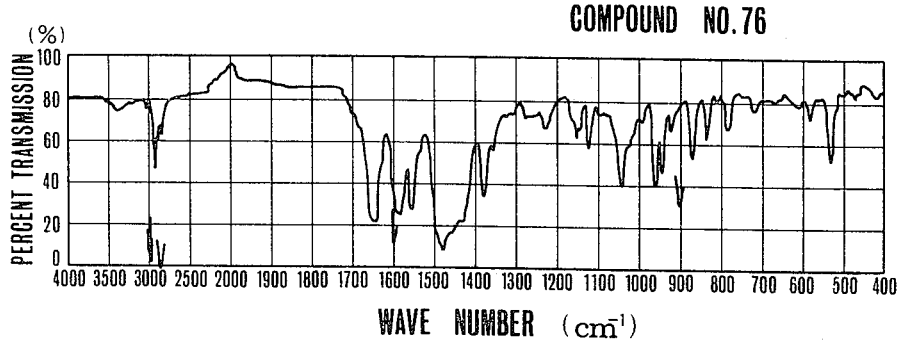
FIG.28 COMPOUND NO.76
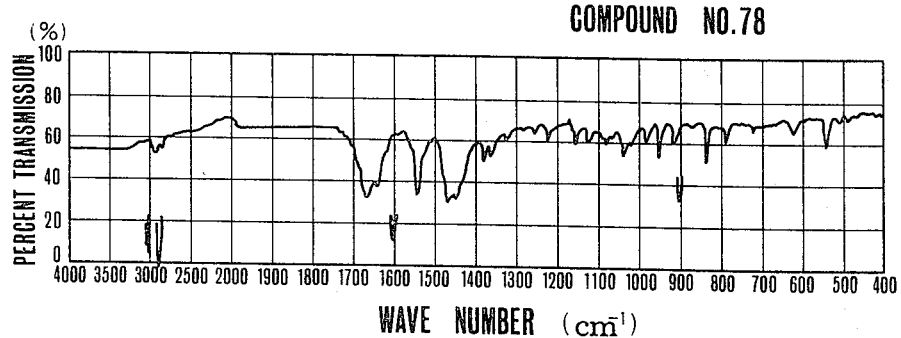
FIG.29 COMPOUND NO.78
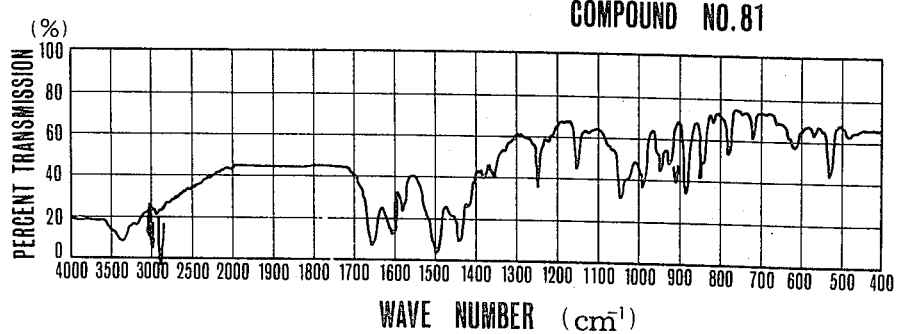
FIG.30 COMPOUND NO.81

HERBICIDAL COMPOSITION OF 3,4-DIHYDRO-2H-PYRANE-2,4-DIONES AND METHODS

This is a division of U.S. Patent application Ser. No. 406,621 filed Oct. 15, 1973, now U.S. Pat. No. 3,927,034.

The present invention relates to novel compounds of 3,4-dihydro-2H-pyrane-2,4-diones, the process for the preparation thereof and their uses as herbicides having selective activity and plant growth regulator.

Further, this invention relates to herbicidal and plant growth regulating compositions containing one or more of novel compounds, and to the method of combatting weeds and regulating the plant growth which comprises applying to plant or to soil the said compounds.

In addition to the above-mentioned effects the compounds of the present invention show both acaricidal and fungicidal activities.

It is an object of the present invention to prepare new 3,4-dihydro-2H-pyrane-2,4-diones and metal salts thereof.

Another object is to prepare improved compositions and processes for killing undesired plants.

The inventors synthesized quite a few compound of 3,4-dihydro-2H-pyrane-2,4-diones derivatives and tested the biological activities for the compounds.

As the result of the test, it has been discovered that the new and novel compounds of the present invention are particularly effective as herbicides and plant growth regulators.

The novel compounds of this invention are characterized by the following formula:

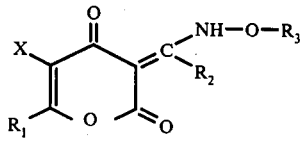

wherein X is hydrogen or halogen;
$R_1$ is alkyl having six or less carbon atoms or phenyl;
$R_2$ is alkyl having 1 to 20 carbon atoms or alkyl having 1 to 20 carbon atoms substituted with halogen or phenyl or phenyl substituted with halogen or nitro or benzyl or phenoxymethyl or 2-phenylvinyl;
$R_3$ is hydrogen or alkyl having 1 to 10 carbon atoms or alkenyl having 6 or less carbon atoms or alkynyl having 6 or less carbon atoms or benzyl; a proviso, $R_1$ and $R_2$ does not represent simultaneously methyl group and metal salts of the above formula compounds.

However, it is expected that the compound of the present invention has the following three chemical formulae because of it's tautomerism

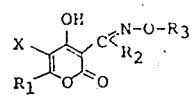 , 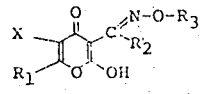 , 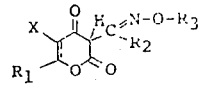

The compounds are particularly effective as selective herbicides for grass weeds such as annual bluegrass (Poa annua), water foxtail (Alopecurus aequalis), large crab-grass (Digitaria adscendens) and others in both soil treatment and foliar treatment, especially it has now been found that the compounds hardly injure leguminous plants such as adzuki bean (phaseolus angularis) and soy bean (Glycine max) and broad leaf plants such as sugar beets which easily suffer phyto-toxicity.

It is already known that 4-hydroxy-6-methyl-α-piron derivatives has herbicidal properties as shown in Japanese Patent Publication No. 16916/1971.

But in order to wither completely to death the said grass weeds, a large amount of the above herbicidal chemical is required and this is one drawback for above mentioned herbicidal agent.

In the other words, according to the descriptions of above mentioned public patent bulletin and the results of the later additional experiments by the inventors, a chemical amount containing 500 g of effective component, in proportion to 10 a. of area is able to give an expected effect in the case of employing it practically, but another chemical amount containing 250 g of effective component, in proportion to 10 a. of area is not able to wither all miscellaneous grasses to death, in the other words, it cannot give a perfect herbicidal effect.

But, in the event of employing the compound of the present invention as a herbicidal agent, a chemical amount containing 250 g of effective component, as a matter of course, further a chemical amount containing 125 g or less of effective component, in proportion to 10 a. of area, in compliance with the same treating method of conventional herbicidal agents indicates a strong herbicidal effect and thereby a perfect herbal prevention and extermination can be expected.

As a surprising matter, some kind of the compound by the present invention in the event of applying it to barnyard grass with a soil treatment by water stagnation indicates 30 multiples or more of herbicidal effect, in comparison with the effect of above mentioned conventional compounds.

In case of foliar treatment using the compounds of the present invention, even the same amount of chemical which makes barnyard grass of grass weed completely kill gives no damages to broadleaf plants such as radish, soy bean (Glycine max), garden pea (Pisum sativum), spinach (Spinacia oleracea) and sugar beets at all, and in case of soil treatment before germination, even the same amount of chemicals which prevents large crab-grass (Digitaria adscendens) germinating gives no damages to seeds of broad leaf plants at all.

As mentioned above, a secure safety to the broadleaf crop against phytotoxicity of the herbicidal agent is extremely high and as to its application, in the other words, its applicable period, its applying location and its applying concentration, it has a very broad extent and it can be used in the wider extent.

It has been further found that the new compounds of the present invention have both dwarfing effect which control the excess growth of perennial plant, particularly lawn and inhibition effect of heading.

Though lawn which is one of industrial crops is widely grown in gardens and golf rinks, it is very troublesome to trim it well, particularly in summer lawn grows well, a large labor power is employed for mowing it and further heading spoils remarkably it's beautiful sight.

The compounds of the said general formula can be applied to the soil or leaves, and show the drawfing effects, inhibitions of heading and runner for lawn without injury.

The compounds of the present invention shows plant growth regulating effect of controlling the growth of new buds without giving any damages to developing leaves and stems of broad leaf crops when the compounds are used in greater quantities than the compounds are used to have the effects of killing weeds and the activity of selective herbicides for broad leaf crops.

Growth inhibiting effect for new buds of broad leaf crops prevents sucker growth of tobacco or chrysanthemum, stops useless nutritive growth of fruit-trees or beans and further change the said growth to reproductive growth. These controlling effects are very useul for cultivating crops.

It is another advantage of the present invention that a residual toxicity in the soil or the plant and an acute toxicity for warm blooded animals and fishes are not feared because the said compounds can be employed with a low chemical concentration.

The invention will be more readily understood from the following detailed description and the accompanying drawings, in which:

FIGS. 1 through 30 show infrared spectrums for some of the compounds described herein.

The compounds of this invention can be prepared in accordance with the following equation;

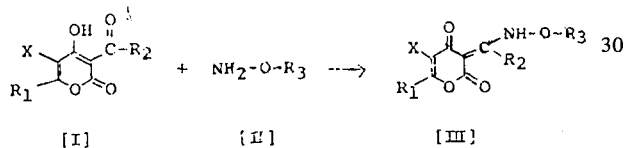

[I]     [II]     [III]

wherein $R_1$, $R_2$, $R_3$ and X represent the aforesaid meanings.

In practical method the compounds of this invention are prepared through the reaction of general formula (I) with the general formula (II) in inert solvent.

As an inert solvent, acetone, ether, methylalcohol, ethylalcohol, isopropylalcohol, benzene, dimethylformamide chloroform, acetonitrile, dichloroethane, dichloromethane, ethyl acetate dioxane, toluene, xylene and dimethyl sulfoxide etc. are used, but preferably methylalcohol, ethylalcohol, isopropylalcohol, acetonitrile, dimethylformamide, dioxane, ether and chloroform are used.

Reaction temperature is from $-10°$ C to the boiling point of employed solvent, preferably from 10 to 30 and the reaction terminates between 0.5 and several hours.

Furthermore a little amount of toluenesulfonic acid, hydrogen chloride gas and Lewice acids such as trifluoroboron and aluminum chloride can be added as a catalyst, if necessary.

After the reaction terminated, the solvent, if necessary, is replaced and then, the reaction mixture is extracted with an alkaline solution and further, an alkaline layer is acidified with hydrochloric acid, whereby the crude product is isolated from the reaction mixture by extraction with solvent or by filtration.

In case of crystaline substance, the crude product can be purified by recrystallization and in oily substance the crude product can be purified by distillation or isolation by column chromatography.

A chemical structure for the resulting purified compound can be confirmatively identified by means of an elementary analysis, NMR spectrum and IR spectrum.

In the case of producing the metal salt of the compound by the present invention, above mentioned compound having the said formula [III] is homogeneously mixed with caustic soda or caustic potassium in the presence of an organic solvent such as acetone, methaol, ethanol, or dimethylformamide and both components are made to react each other, if necessary, by means of heating step and thereby the sodium salt or the potassium salt can be obtained. Further, if the said sodium salt or the said potassium salt is made to react similarly with other kinds of above mentioned metal salt, the objective metal salt can be obtained. In numerous cases, the said metal salt is sedimented as a precipitate or as a crystal in above mentioned solvent.

Some metal salt of the present invention produced with above mentioned process may cause partially a chemical change or a decomposition at a high temperature, so that it does not show a clear melting point. Therefore, by applying Infrared ray absorptive spectrum to the raw material and the reaction compound, a formation of the metal salt can be identified through a transference of absorption band and a change of absorption intensity. In the other words, the raw material compound having the said general formula [I] indicates an absorption of carbonyl group at a wavelength range of 1720 to 1730 $cm^{-1}$, whereas the corresponded metal salt shows the absorption at a side of longer wavelength. Further, in some occasion, an anion such as $OH^-$ may be simultaneous coordinated with a metal atom of some metal salt obtained above.

In order to facilitate a clear understanding of the invention, the following preferred specific embodiments are described as illustrative and not as limiting the invention.

Example 1:

Process for producing 3-[1-(N-allyloxyamino)propylidene]-6-methyl-3,4-dihydro-2H-pyran-2,4-dione 1.8 g (0.01 mol) of 4-hydroxy-6-methyl-3-propionyl-$\alpha$-pyrane was dissolved in 10 c.c. of ethanol and 0.8 g (0.011 mol) of allyloxy amine was added in the resulting solution and then, it was agitated during two hours at room temperature. Further, it was agitated during 30 minutes at a temperature of about 70° – 80° C and then ethanol was distilled off from it under a reduced pressure and a residue was dissolved in chloroform. The resulting chloroform solution was extracted for two times with a caustic soda solution having 5 % of concentration by an amount of 7 – 8 c.c. and an alkaline layer produced thereto was hydrochlorinated and thereby, an oleo-material was visibly sedimented. The said oleo-material was extracted for two times with 10 c.c. of chloroform and the resulting chloroform layer produced thereto was rinsed with water and it was dried with magnesium sulfate. The resulting chloroform was distilled off under a reduced pressure and thereby 2 g of 3-[1-(N-allyloxyamino)propylidene]-6-methyl-3,4-dihydro-2H-pyran-2,4-dione, indicating colorless oily was obtained with 84 % of yield rate. Refractive index : $n_D^{28}$ 1.5311. Elementary analysis (%).

Found: C, 60.70; H, 6.35; N, 5.96;
Calculated for $C_{12}H_{15}NO_4$: C, 60.75; H, 6.37; N, 5.90

Example 2:

Process for producing [1-(N-allyloxyamino)butylidene]-6-methyl-3,4-dihydro-2H-pyran-2,4-dione 3.0 g (0.015 mole) of 3-butyryl-4-hydroxy-6-methyl-α-pyrone was dissolved in 20 c.c. of ethanol and further, 1.2 g (0.017 mol) of allyloxyamine was added in it and the resulting solution was continuously agitated firstly at a room temperature during two hours and secondly at a temperature of about 70° – 80° C during 30 minutes.

After having carried out a cooling step for it, ethanol was distilled off from it under a reduced pressure and a residue was dissolved in chloroform and the resulting chloroform solution was extracted for two times with 15 c.c. of caustic soda having 5 % of concentration. A resulting alkaline layer produced thereto was hydrochlorinated and a resulting sedimented material was extracted with 15 c.c. of chloroform and a resulting chloroform layer was rinsed with water and then, it was dried with magnesium sulfate. Then, the chloroform layer was distilled off and a residual material was recrystallized with n-hexane and thereby 2.8 g of 3-[1-(N-allyloxyamino)butylidene]-6-methyl-3,4-dihydro-2H-pyran-2,4-dione, as a colorless crystal was obtained with 74 % of yield rate.

Melting point: 52° – 54° C.
Elementary analysis (%):
Found: C, 62.10; H, 6.83; N, 5.61;
Calculated for $C_{13}H_{17}NO_4$: C, 62.14; H, 6.82; N, 5.57

Example 3:

Process for producing 3-[1-(N-ethoxyamino)propylidene]-6-ethyl-3,4-dihydro-2H-pyran-2,4-dione 2.0 g (0.01 mol) of 6-ethyl-4-hydroxy-3-propionitrile-α-pyrone and 0.66 g (0.011 mol) of ethoxyamine were employed and the same reaction operation in Example 2 was carried out and thereby, 2.0 g of 3-[1-(N-ethoxyamino)propylidene]-6-ethyl-3,4-dehydro-2H-pyran-dione, as a colorless crystal, was obtained with 83.0 % of yield rate.

Melting point: 54° – 55° C.
Elementary analysis (%):
Found: C, 60.19; H, 7.10; N, 5.90;
Calculated for $C_{12}H_{17}NO_4$: C, 60.25; H, 7.11; N, 5.86

Example 4:

Process for producing 3-[1-(N-ethoxyamino)butylidene]-6-propyl-3,4-dihydro-2H-pyran-2,4-dione 2.2 g (0.01 mol) of 3-butyryl-4-hydroxy-6-propyl-α-pyrone and 0.66 g (0.011 mol) of ethoxyamine were employed and the same reaction operation in Example 1 was carried out and thereby, 2.5 g of 3-[1-ethoxyamino)butylidene]-6propyl-3,4-dihydro-2H-pyran-2,4-dione as a yellowish oleo-material was obtained with 94 % of yield rate.

Refractive index: $n^{24.5}$ 1.5168
Elementary analysis (%):
Found: C, 62.87; H, 7.90; N, 5.31;
Calculated for $C_{14}H_{21}NO_4$: C, 62.90; H, 7.92; N, 5.24

Example 5

Process for producing 5-bromo-3-[1-(N-ethoxyamino)-propylidene]-6-ethyl-3,4-dihydro-2H-pyran-2,4-dione 1.4 g of 5-bromo-6-ethyl-4-hydroxy-3-propionyl-pyrone (a melting point of 76.5° C to 77.5° C) was dissolved in 10 c.c. of ethanol and further 0.5 g of ethoxyamine was added in it and the resulting solution was agitated at room temperature during 4 hours. Further, it was agitated at a temperature of 40°–50° C during 30 minutes. Then, above ethanol was distilled off from the resulting reaction mixture under a reduced pressure and thereby, a crude white crystal was obtained. Further, the crude white crystal was recrystallized by using n-hexane and thus, a white spicular crystal was obtained as an objective compound.

Melting point: 46°– 47° C
Yield amount: 1.3 g (Yield rate: 81 %)

Example 6

Process for producing 5-bromo-3-[1-(N-allyloxyamino)-butylidene]-6-propyl-3,4-dihydro-2H-pyran-2,4-dione 1.5 g of 5-bromo-3-butyl-4-hydroxy-6-propyl-α-pyrone (a melting point of 50°–51° C) was dissolved in 10 c.c. of ethanol and 0.6 g allyloxyamine was added in it and the resulting solution was agitated at room temperature during 4 hours and further, it was continuously agitated at a temperature of 40°–50° C during 30 minutes. Then, above ethanol was distilled off from above resulting solution under a reduced pressure and thereby, a colorless, viscous liquid was obtained. The said colorless, viscous liquid was dissolved in 10 c.c. of ether and this solution was extracted for 2 time with 20 c.c. of aqueous solution containing 5 % concentration of caustic soda. Then, the resulting caustic soda solution was acidified with concentrated hydrochloric acid under cooling conditions and thereby an oleo material was sedimented in it.

The said oleo-material was separated from the solution and it was extracted for 2 times with 10 c.c. of ether and an ether layer obtained thereto was rinsed with water. The said ether layer was dried with magnesium sulfate and then, the ether layer was distilled off under a reduced pressure and thus, a light yellowish oleo-material was obtained as an objective material.

Refractive index: $n_D^{24}$ 1.5535
Yield amount 1.6 g (Yield rate: 93 %)

Example 7:

Sodium salt of 3-(1-N-allyloxyaminobutylidene)-6-methyl-3,4-dihydro-2H-pyran-2,4-dione 2.5 g of 3-(1-N-allyloxyaminobutylidene)-6-methyl-3,4-dihydro-2H-pyran-2,4-dione were dissolved in 20 cc of acetone, and to which 0.4 g of sodium hydroxide dissolved in 2 cc of water was added gradually under agitation at room temperature. White crystal of sodium salt were obtained. Yield 2.7 g (100 %)

m.p. 114°–116° C
infrared spectrum: 1660 $cm^{-1}$ (C=O)

Example 8:

Nickel salt of 3-(1-N-ethoxyaminopropylidene)-6-methyl-3,4-dihydro-2H-pyran-3,4-dione 2.3 g of 3-(1-N-ethoxyaminopropylidene)-6-methyl-3,4-dihydro-2H-pyran-3,4-dione were dissolved in 20 cc of acetone and to which 0.4 g of sodium hydroxide dissolved in 2 cc of water was added under agitation. Agitation was continued for 10 min., to the reaction mixture 1.2 g of nickel chloride ($NiCl_2 6H_2O$) dissolved in 2 cc of water was added under agitation. Green crystal of nickel salt were obtained. Yield 2.4 g (95 %)
m.p. 218°–219° C (with decomposition)
infrared spectrum (C=O) 1683 $cm^{-1}$

Example 9:

Copper$^{(+2)}$ salt of 3-(1-N-ethoxyaminopropylidene)-6-ethyl-3,4-dihydro-2H-pyran-2,4-dione By a procedure in similar to Example 8, from the reaction of 2.4 g of Copper$^{(+2)}$ salt of 3-(1-N-ethoxyaminopropylidene)-6-ethyl-3,4-dihydro-2H-pyran-2,4-dione, 0.4 g of sodium hydroxide and 1.25 g of copper sulfate ($CuSO_4.5H_2O$), dark agreen crystals of copper salt were obtained. Yield 2.7 g (100 %)
m.p. 172°–174° C (with decomposition)
infrared spectrum: 1673 $cm^{-1}$ (C=O)

Example 10.

Barium salt of 3-(1-N-ethoxyaminopropylidene)-6-ethyl-3,4-dihydro-2H-pyran-2,4-dione By a similar procedure to Example 8, from the reaction of 2.4 g of 3-(1-N-ethoxyaminopropylidene)-6-ethyl-3,4-dihydro-2H-pyran-2,4-dione, 0.4 g of sodium hydroxide and 1.2 g of barium chloride ($BaCl_2.2H_2O$), crude crystals were obtained.

The crude crystals were dissolved in 99.5 % ethanol and unsoluble substances were taken away from it, 2.8 g. of white dust crystal was obtained with 90 % of yield rate.
m.p. over 300° C
infrared spectrum: 1673 $cm^{-1}$ (c=o)

In addition to the above mentioned compound described in the preceding examples, some typical compounds of the present invention are listed in Table 1.

Table 1

| Compound No. | Chemical Name | Physical Constant |
|---|---|---|
| 1 | 3-(1-N-ethoxyaminopropylidene)-6-methyl-3,4-dihydro-2H-pyran-2,4-dione | m.p. 57 – 58° C |
| 2 | 3-(1-N-allyloxyaminopropylidene)-6-methyl-3,4-dihydro-2H-pyran-2,4-dione | refractive index $n_D^{25}$ 1.5720 |
| 3 | 3-(1-N-ethoxyaminobutylidene)-6-methyl-3,4-dihydro-2H-pyran-2,4-dione | m.p. 38 – 40° C |
| 4 | 3-(1-N-allyloxyaminobutylidene)-6-methyl-3,4-dihydro-2H-pyran-2,4-dione | m.p. 52 – 54° C |
| 5 | 3-(1-N-ethoxyaminopentylidene)-6-methyl-3,4-dihydro-2H-pyran-2,4-dione | m.p. 36 – 38° C |
| 6 | 3-(1-N-allyloxyaminopentylidene)-6-methyl-3,4-dihydro-2H-pyran-2,4-dione | refractive index $n_D^{26.5}$ 1.5299 |
| 7 | 3-(1-N-ethoxyamino-2,2-dimethylpropylidene)-6-methyl-3,4-dihydro-2H-pyran-2,4-dione | m.p. 177 – 178° C |
| 8 | 3-(1-N-allyloxyamino-2,2-dimethylpropylidene)-6-methyl-3,4-dihydro-2H-pyran-2,4-dione | m.p. 127 – 129° C |
| 9 | 3-(1-N-ethoxyaminohexylidene)-6-methyl-3,4-dihydro-2H-pyran-2,4-dione | m.p. 55 – 56° C |
| 10 | 3-(1-N-allyloxyaminohexylidene)-6-methyl-3,4-dihydro-2H-pyran-2,4-dione | refractive index $n_D^{28}$ 1.5236 |
| 11 | 3-(1-N-ethoxyaminodecylidene)-6-methyl-3,4-dihydro-2H-pyran-2,4-dione | refractive index $n_D^{28}$ 1.5053 |
| 12 | 3-(1-N-allyloxyaminodecylidene)-6-methyl-3,4-dihydro-2H-pyran-2,4-dione | refractive index $n_D^{28}$ 1.5135 |
| 13 | 3-(1-N-allyloxyaminododecylidene)-6-methyl-3,4-dihydro-2H-pyran-2,4-dione | m.p. 36 – 38° C |
| 14 | 3-(1-N-allyloxyaminohexadecylidene)-6-methyl-3,4-dihydro-2H-pyran-2,4-dione | m.p. 48 – 49° C |
| 15 | 3-(1-N-allyloxyaminooctadecylidene)-6-methyl-3,4-dihydro-2H-pyran-2,4-dione | m.p. 54 – 56° C |
| 16 | 3-(1-N-ethoxyamino-4-chlorobutylidene)-6-methyl-3,4-dihydro-2H-pyran-2,4-dione | refractive index $n_D^{29.5}$ 1.5342 |
| 17 | 3-(1-N-allyloxyamino-4-chlorobutylidene)-6-methyl-3,4-dihydro-2H-pyran-2,4-dione | refractive index $n_D^{26}$ 1.5377 |
| 18 | 3-(1-N-ethoxyaminobenzylidene)-6-methyl-3,4-dihydro-2H-pyran-2,4-dione | m.p. 184 – 185° C (with decomposition) |
| 19 | 3-(1-N-allyloxyaminobenzylidene)-6-methyl-3,4-dihydro-2H-pyran-2,4-dione | m.p. 142 – 144° C |
| 20 | 3-(1-N-allyloxyamino-p-chlorobenzylidene)-6-methyl-3,4-dihydro-2H-pyran-2,4-dione | m.p. 139 – 141° C |
| 21 | 3-(1-N-allyloxyamino-p-nitrobenzylidene)-6-methyl-3,4-dihydro-2H-pyran-2,4-dione | m.p. 142 – 143° C |
| 22 | 3-(1-N-ethoxyamino-2-phenylethylidene)-6-methyl-3,4-dihydro-2H-pyran-2,4-dione | refractive index $n_D^{28.5}$ 1.5754 |
| 23 | 3-(1-N-ethoxyamino-2-phenoxyethylidene)-6-methyl-3,4-dihydro-2H-pyran-2,4-dione | m.p. 93 – 94° C |
| 24 | 3-(1-N-ethoxyaminocinnamylidene)-6-methyl-3,4-dihydro-2H-pyran-2,4-dione | m.p. 65 – 66° C (with decomposition) |
| 25 | 3-(1-N-allyloxyaminocinnamylidene)-6-methyl-3,4-dihydro-2H-pyran-2,4-dione | refractive index $n_D^{25}$ 1.5839 |
| 26 | 3-(1-N-allyloxyaminoethylidene)-6-ethyl-3,4-dihydro-2H-pyran-2,4-dione | m.p. 39.5 – 40° C |
| 27 | 3-(1-N-hydroxyaminopropylidene)-6-ethyl-3,4-dihydro-2H-pyran-2,4-dione | m.p. 161 – 162° C (with decomposition) |
| 28 | 3-(1-N-methoxyaminopropylidene)-6-ethyl-3,4-dihydro-2H-pyran-2,4-dione | m.p. 43 – 44° C |
| 29 | 3-(1-N-ethoxyaminopropylidene)-6-ethyl-3,4-dihydro-2H-pyran-2,4-dione | m.p. 54 – 55° C |
| 30 | 3-(1-N-propoxyaminopropylidene)-6-ethyl-3,4-dihydro-2H-pyran-2,4-dione | refractive index $n_D^{22}$ 1.5315 |
| 31 | 3-(1-N-isopropoxyaminopropylidene)-6-ethyl-3,4-dihydro-2H-pyran-2,4-dione | m.p. 44 – 46° C |
| 32 | 3-(1-N-allyloxyaminopropylidene)-6-ethyl-3,4-dihydro-2H-pyran-2,4-dione | refractive index $n_D^{26.5}$ 1.5389 |
| 33 | 3-(1-N-propargyloxyaminopropylidene)-6-ethyl-3,4-dihydro-2H-pyran-2,4-dione | m.p. 84 – 86° C |
| 34 | 3-(1-N-n-butoxyaminopropylidene)-6-ethyl-3,4-dihydro-2H-pyran-2,4-dione | refractive index $n_D^{18}$ 1.5169 |
| 35 | 3-(1-N-hexyloxyaminopropylidene)-6-ethyl-3,4-dihydro-2H-pyran-2,4-dione | refractive index $n_D^{22.5}$ 1.5170 |
| 36 | 3-(1-N-benzyloxyaminopropylidene)-6-ethyl-3,4-dihydro-2H-pyran-2,4-dione | m.p. 63 – 65° C |
| 37 | 3-(1-N-ethoxyaminobutylidene)-6-ethyl-3,4-dihydro-2H-pyran-2,4-dione | refractive index $n_D^{26}$ 1.5199 |

Table 1-continued

| Compound No. | Chemical Name | Physical Constant |
|---|---|---|
| 38 | 3-(1-N-allyloxyaminobutylidene)-6-ethyl-3,4-dihydro-2H-pyran-2,4-dione | refractive index $n_D^{26}$ 1.5310 |
| 39 | 3-(1-N-ethoxyaminobenzylidene)-6-ethyl-3,4-dihydro-2H-pyran-2,4-dione | m.p. 133 – 135° C (with decomposition) |
| 40 | 3-(1-N-allyloxyaminobenzylidene)-6-ethyl-3,4-dihydro-2H-pyran-2,4-dione | m.p. 118 – 120° C |
| 41 | 3-(1-N-ethoxyaminoethylidene)-6-n-propyl-3,4-dihydro-2H-pyran-2,4-dione | m.p. 57 – 58° C |
| 42 | 3-(1-N-ethoxyaminopropylidene)-6-n-propyl-3,4-dihydro-2H-pyran-2,4-dione | refractive index $n_D^{25.5}$ 1.5265 |
| 43 | 3-(1-N-allyloxyaminopropylidene)-6-n-propyl-3,4-dihydro-2H-pyran-2,4-dione | refractive index $n_D^{25.5}$ 1.5330 |
| 44 | 3-(1-N-ethoxyaminobutylidene)-6-n-propyl-3,4-dihydro-2H-pyran-2,4-dione | refractive index $n_D^{24.5}$ 1.5168 |
| 45 | 3-(1-N-allyloxyaminobutylidene)-6-n-propyl-3,4-dihydro-2H-pyran-2,4-dione | refractive index $n_D^{24.5}$ 1.5300 |
| 46 | 3-(1-N-ethoxyaminobenzylidene)-6-n-propyl-3,4-dihydro-2H-pyran-2,4-dione | m.p. 153 – 154° C |
| 47 | 3-(1-N-allyloxyaminobenzylidene)-6-n-propyl-3,4-dihydro-2H-pyran-2,4-dione | m.p. 125 – 126° C |
| 48 | 3-(1-N-allyloxyaminopropylidene)-6-i-propyl-3,4-dihydro-2H-pyran-2,4-dione | refractive index $n_D^{24}$ 1.5360 |
| 49 | 3-(1-N-ethoxyaminopentylidene)-6-n-butyl-3,4-dihydro-2H-pyran-2,4-dione | refractive index $n_D^{22}$ 1.5148 |
| 50 | 3-(1-N-ethoxyaminopropylidene)-6-i-butyl-3,4-dihydro-2H-pyran-2,4-dione | refractive index $n_D^{22.5}$ 1.5259 |
| 51 | 3-(1-N-allyloxyaminopropylidene)-6-i-butyl-3,4-dihydro-2H-pyran-2,4-dione | refractive index $n_D^{22.5}$ 1.5328 |
| 52 | 3-(1-N-ethoxyamino-3-methylbutylidene)-6-i-butyl-3,4-dihydro-2H-pyran-2,4-dione | refractive index $n_D^{19}$ 1.5173 |
| 53 | 3-(1-N-ethoxyaminoethylidene)-6-phenyl-3,4-dihydro-2H-pyran-2,4-dione | m.p. 111 – 113° C |
| 54 | 3-(1-N-ethoxyaminopropylidene)-6-phenyl-3,4-dihydro-2H-pyran-2,4-dione | m.p. 80 – 81° C |
| 55 | 3-(1-N-allyloxyaminopropylidene)-6-phenyl-3,4-dihydro-2H-pyran-2,4-dione | m.p. 101 – 102° C |
| 56 | 3-(1-N-ethoxyaminobutylidene)-6-phenyl-3,4-dihydro-2H-pyran-2,4-dione | m.p. 77 – 79° C |
| 57 | 3-(1-N-allyloxyaminobutylidene)-6-phenyl-3,4-dihydro-2H-pyran-2,4-dione | m.p. 64 – 66° C |
| 58 | 3-(1-N-ethoxyaminobenzylidene)-6-phenyl-3,4-dihydro-2H-pyran-2,4-dione | m.p. 172 – 174° C (with decomposition) |
| 59 | 3-(1-N-allyloxyaminobenzylidene)-6-phenyl-3,4-dihydro-2H-pyran-2,4-dione | m.p. 175 – 176° C (with decomposition) |
| 60 | 3-(1-N-allyloxyaminopropylidene)-5-bromo-6-methyl-3,4-dihydro-2H-pyran-2,4-dione | m.p. 47 – 47.5° C |
| 61 | 3-(1-N-ethoxyaminobutylidene)-5-bromo-6-methyl-3,4-dihydro-2H-pyran-2,4-dione | refractive index $n_D^{24}$ 1.5439 |
| 62 | 3-(1-N-allyloxyaminobutylidene)-5-bromo-6-methyl-3,4-dihydro-2H-pyran-2,4-dione | refractive index $n_D^{24}$ 1.5512 |
| 63 | 3-(1-N-ethoxyaminopropylidene)-5-bromo-6-ethyl-3,4-dihydro-2H-pyran-2,4-dione | m.p. 46 – 47° C |
| 64 | 3-(1-N-allyloxyaminopropylidene)-5-bromo-6-ethyl-3,4-dihydro-2H-pyran-2,4-dione | refractive index $n_D^{20.5}$ 1.5690 |
| 65 | 3-(1-N-ethoxyaminobutylidene)-5-bromo-6-n-propyl-3,4-dihydro-2H-pyran-2,4-dione | refractive index $n_D^{24}$ 1.5488 |
| 66 | 3-(1-N-allyloxyaminobutylidene)-5-bromo-6-n-propyl-3,4-dihydro-2H-pyran-2,4-dione | refractive index $n_D^{24}$ 1.5535 |
| 67 | Nickel salt of 3-(1-N-ethoxyaminopropylidene)-6-methyl-3,4-dihydro-2H-pyran-2,4-dione | m.p. 218 – 219° C (with decomposition) |
| 68 | Sodium salt of 3-(1-N-allyloxyaminobutylidene)-6-methyl-3,4-dihydro-2H-pyran-2,4-dione | m.p. 114 – 116° C |
| 69 | Nickel salt of 3-(1-N-allyloxyaminobutylidene)-6-methyl-3,4-dihydro-2H-pyran-2,4-dione | m.p. 217 – 218° C (with decomposition) |
| 70 | Copper$^{(+2)}$ salt of 3-(1-N-allyloxyaminobutylidene)-6-methyl-3,4-dihydro-2H-pyran-2,4-dione | m.p. 138 – 139° C |
| 71 | Zinc monohydroxide salt of 3-(1-N-allyloxyaminobutylidene)-6-methyl-3,4-dihydro-2H-pyran-2,4-dione | m.p. 300° C up |
| 72 | Calcium salt of 3-(1-N-ethoxyaminopropylidene)-6-ethyl-3,4-dihydro-2H-pyran-2,4-dione | m.p. 300° C up |
| 73 | Barium salt of 3-(1-N-ethoxyaminopropylidene)-6-ethyl-3,4-dihydro-2H-pyran-2,4-dione | m.p. 300° C up |
| 74 | Mangane$^{(+2)}$ salt of 3-(1-N-ethoxyaminopropylidene)-6-ethyl-3,4-dihydro-2H-pyran-2,4-dione | m.p. 300° C up |
| 75 | Iron$^{(+2)}$ salt of 3-(1-N-ethoxyaminopropylidene)-6-ethyl-3,4-dihydro-2H-pyran-2,4-dione | m.p. 144 – 145° C (with decomposition) |
| 76 | Cobalt salt of 3-(1-N-ethoxyaminopropylidene)-6-ethyl-3,4-dihydro-2H-pyran-2,4-dione | m.p. 218 – 219° C (with decomposition) |
| 77 | Nickel salt of 3-(1-N-ethoxyaminopropylidene)-6-ethyl-3,4-dihydro-2H-pyran-2,4-dione | m.p. 223 – 224° C (with decomposition) |
| 78 | Copper$^{(+2)}$ salt of 3-(1-N-ethoxyaminopropylidene)-6-ethyl-3,4-dihydro-2H-pyran-2,4-dione | m.p. 172 – 174° C (with decomposition) |
| 79 | Silver salt of 3-(1-N-ethoxyaminopropylidene)-6-ethyl-3,4-dihydro-2H-pyran-2,4-dione | m.p. 132 – 135° C (with decomposition) |
| 80 | Sodium salt of 3-(1-N-isopropoxyaminopropylidene)-6-ethyl-3,4-dihydro-2H-pyran-2,4-dione | m.p. 125 – 128° C (with decomposition) |
| 81 | Calcium salt of 3-(1-N-allyloxyaminopropylidene)-6-ethyl-3,4-dihydro-2H-pyran-2,4-dione | m.p. 300° C up |
| 82 | Copper$^{(+2)}$ salt of 3-(1-N-ethoxyaminobutylidene)-6-propyl-3,4-dihydro-2H-pyran-2,4-dione | m.p. 151 – 152° C |

Hereinafter, the compounds of this invention are represented by Compound No. in Table 1.

The compounds of this invention can be applied directly to the soil as pre-emergence treatment or as post-emergence treatment and to plant foilage or they can be mixed intimately with the soil and may be applied to soil or foliar at rates of 50–1000 g per area, preferably 100–500 g per area, more preferably 200–300 g per area.

The method of the present invention comprehends the employment of a liquid or solid composition containing one or more of the present compounds as an active component.

The active ingredient of this invention may be formulated by mixing with suitable carriers in a form generally used in agricultural chemicals such as wettable powder, emulsifiable concentrate, dust formulation, granular formulation, water soluble powder and aerosol. As solid carriers, bentonite, diatomaceous earth, apatite, gypsum, talc, pyrophyllite, vermiculite, clay and others are used. As liquid carriers, kerosene, mineral oil, petroleum, solvent naphtha, benzene, xylene, cyclohexane, cyclohexanone, dimethylformamide, alcohol, acetone, and others are used. Sometimes surface active agent is added in order to give a homogeneous and stable formulation.

The compounds of this invention also can be applied admixed with other chemicals which are used in agronomic and horticultural management and are compatible with the compounds of this invention. Such chemicals can be, but are not restricted to, the classes of chemicals commonly known as plant nutrients, fertilizers, insecticides acaricides, fungicides, herbicides and nematocides.

The concentrations of the active ingredients in the herbicidal and plant growth regulating compositions of this invention vary according to type of formulation, and they are, for example, used in a range of 5–80 weight percent, preferably 20–80 weight percent, in wettable powders, 5–70 weight percent, preferably 10–50 weight percent, in emulsifiable concentrates, and 0.5–20 weight percent, preferably 1–10 weight percent in dust formulation.

Thus, a wettable powder or an emulsifiable concentrate produced thereto is diluted with water to a specified concentration and thereby, it is used as a liquid suspension or a liquid emulsion for treating the soils or the foliars leaf. Further, a dust formulation is directly used for the soil treatment or the foliar treatment.

The non-limiting examples for the herbicidal and plant growth regulating compositions are illustrated as follows:

Example 11.

| Wettable Powder | |
|---|---|
| | Parts by weight |
| Compound 1 | 50 |
| Diatomaceous earth | 21 |
| Sodium alkylsulfate | 9 |
| Talc | 20 |

These are mixed homogeneously and reduced to fine particles. Consequently, wettable powder containing 50 % of active ingredient is obtained. In practical use, it is diluted to a certain concentration with water and is sprayed as a suspension.

Example 12.

| Wettable Powder | |
|---|---|
| | Parts by weight |
| Compound 2 | 30 |
| Diatomaceous earth | 35 |
| Sodium alkylsulfate | 9 |
| Talc | 26 |

These are mixed homogeneously and reduced to fine particles. Consequently, wettable powder containing 30 % of active ingredient is obtained. In practical use, it is diluted to a certain concentration with water and is sprayed as a suspension.

Example 13.

| Emulsifiable Concentrate | |
|---|---|
| | Parts by weight |
| Compound 3 | 25 |
| xylene | 50 |
| dimethylformamide | 13 |
| polyoxyethylene phenylether | 12 |

These are mixed and dissolved.

Consequently, emulsifiable concentrate containing 25 % of the active ingredient is obtained. In practical use, it is diluted to certain concentration with water and then is sprayed as an emulsion.

Example 14.

| Emulsifiable Concentrate | |
|---|---|
| | Parts by weight |
| Compound 4 | 50 |
| xylene | 30 |
| dimethylformamide | 12 |
| polyoxyethylene phenylether | 8 |

These are mixed and dissolved.

Consequently, emulsifiable concentrate containing 50 % of the active ingredient is obtained. In practical use, it is diluted to certain concentration with water and then is sprayed as an emulsion.

Example 15.

| Dust Formulation | |
|---|---|
| | Parts by weight |
| Compound 5 | 10 |
| Talc | 38 |
| Bentonite | 10 |
| Clay | 37 |
| Sodium alkylsulfate | 5 |

These are mixed homogeneously and micronized to fine particles. Fine particles is made into granules having the diameter in the range of 0.5–1.0 mm by granulator.

Consequently, dust formulation containing 10 % of the active ingredient is obtained. In practival use it is directly applied.

Example 16.

| Dust Formulation | |
|---|---|
| | Parts by weight |
| Compound 6 | 3 |
| Talc | 85 |
| Bentonite | 9 |
| Carboxymethylcellulose | 1 |
| Sodium alkylsulfate | 2 |

These are mixed homogeneously and micronized to fine particles. Fine particles is made into granules having the diameter in the range of 0.5–1.0 mm by granulator.

Consequently, dust formation containing 3 % of the active ingredient is obtained. In practical use it is directly applied.

The compounds listed in Table 1 possess superior herbicidal and plant growth regulating activities compared to known compounds, further acaricidal and fungicidal activities.

Furthermore, it must be stressed that the compounds of this invention having most superior herbicidal activity are one according to the above-mentioned general formula [3] in which X is hydrogen, $R_1$ and $R_2$ are alkyl having 1 to 4 carbon atoms, $R_3$ is alkyl having 1 to 4 carbon atoms or allyl group or propargyl group.

The superior herbicidal, plant growth regulating, acaricidal and fungicidal effects of the novel compounds of this invention are clearly illustrated by the following tests.

As a compound for the comparison, 3-(N-ethoxyacetoimidoyl)-4-hydroxy-6-methyl-α-pyrone for Test 1 – 8 and calcium salt thereof for Test 10 – 13 which is described in the Specification of Japanese Patent Publication No. 16916/1971 were employed.

Test 1.

Preventive test for inhibiting seed germinations of weeds

A soils containing a seed mixture of large crab-grass smooth pigweed and common purslane was packed in a vat having 780 cm² of cross-sectional area. In the event of initiating seed germination of those weeds, test compound was prepared in similar manner to Example 11 and was diluted with water to a specified concentration and a surface of above soils was treated by spraying the diluted agueous suspension upon it. In the course of the 25th day after the spraying treatment, a growth state of weeds was investigated. A judgement standard for the growth state was classified as six grades in a range of 0 – 5 which has the following means:
0: no effect
1: a few slightly burnt spots
2: marked damage to leaves
3: some leaves and parts of stalks partially dead
4: plant partially destroyed
5: plant completely destroyed or no germination
The results were shown in Table 2.

Table 2

| Test Compound No. | Amount of effective component (g/100a.) | Growth state of the miscellaneous grasses | | |
|---|---|---|---|---|
| | | large crab-grass | smooth pigweed | common purslane |
| 1 | 250 | 5 | 2 | 2 |
| | 125 | 5 | 0 | 1 |
| | 62.5 | 5 | 0 | 0 |
| 2 | 250 | 5 | 1 | 2 |
| | 125 | 5 | 0 | 1 |
| | 62.5 | 5 | 0 | 0 |
| 3 | 250 | 5 | 2 | 2 |
| | 125 | 5 | 0 | 1 |
| | 62.5 | 5 | 0 | 0 |
| 4 | 250 | 5 | 2 | 2 |
| | 125 | 5 | 1 | 1 |
| | 62.5 | 5 | 0 | 0 |
| 5 | 250 | 5 | 2 | 1 |
| | 125 | 5 | 0 | 1 |
| | 62.5 | 5 | 0 | 0 |
| 6 | 250 | 5 | 2 | 2 |
| | 125 | 5 | 0 | 0 |
| | 62.5 | 5 | 0 | 0 |
| 26 | 250 | 5 | 2 | 2 |
| | 125 | 5 | 0 | 1 |
| | 62.5 | 4 | 0 | 0 |

Table 2-continued

| Test Compound No. | Amount of effective component (g/100a.) | Growth state of the miscellaneous grasses | | |
|---|---|---|---|---|
| | | large crab-grass | smooth pigweed | common purslane |
| 29 | 250 | 5 | 2 | 2 |
| | 125 | 5 | 0 | 1 |
| | 62.5 | 5 | 0 | 0 |
| 32 | 250 | 5 | 2 | 2 |
| | 125 | 5 | 1 | 1 |
| | 62.5 | 5 | 0 | 0 |
| 37 | 250 | 5 | 2 | 2 |
| | 125 | 5 | 1 | 1 |
| | 62.5 | 5 | 0 | 1 |
| 38 | 250 | 5 | 2 | 2 |
| | 125 | 5 | 0 | 1 |
| | 62.5 | 5 | 0 | 1 |
| 41 | 250 | 5 | 2 | 1 |
| | 125 | 5 | 0 | 0 |
| | 62.5 | 5 | 0 | 0 |
| 42 | 250 | 5 | 0 | 1 |
| | 125 | 5 | 0 | 0 |
| | 62.5 | 4 | 0 | 0 |
| 43 | 250 | 5 | 1 | 1 |
| | 125 | 5 | 1 | 0 |
| | 62.5 | 5 | 0 | 0 |
| 44 | 250 | 5 | 2 | 2 |
| | 125 | 5 | 1 | 1 |
| | 62.5 | 5 | 0 | 0 |
| 45 | 250 | 5 | 1 | 1 |
| | 125 | 5 | 0 | 1 |
| | 62.5 | 5 | 0 | 0 |
| 46 | 250 | 5 | 1 | 1 |
| | 125 | 5 | 0 | 1 |
| | 62.5 | 5 | 0 | 0 |
| The compound for the comparison | 250 | 5 | 0 | 1 |
| | 125 | 3 | 0 | 1 |
| | 62.5 | 1 | 0 | 0 |
| Untreated Soils | — | 0 | 0 | 0 |

Test 2.

Foliar treatment test

The soils was packed in a vat having 780 cm² of cross-sectional area and then, the seeds of large crab-grass and smooth pigweed were sowed and a covering soils was laid softly upon them and those seeds were made to grow in a greenhouse. In the occasion that those plants were grown to a stage of the second leaf period to the fourth leaf period, the test compound was prepared by the similar method of Example 11 and was diluted to a specified concentration with water and the resulting diluted agueous suspension by 100 l/10a. of amount was sprayed over the stem and the leaf of those plants and thereby, the spraying treatment was carried out. In the course of three weeks after spraying, the growth state of the plants was investigated. In compliance with the judging standard for the growth state defined in Test 1, results were set forth in Table 3.

Table 3

| Test Compound No. | Amount of effective component (g/10a.) | Growth state of miscellaneous grasses | |
|---|---|---|---|
| | | large crab-grass | smooth pigweed |
| 1 | 500 | 4 | 0 |
| | 250 | 4 | 0 |
| | 125 | 2 | 0 |
| 2 | 500 | 4 | 0 |
| | 250 | 3 | 0 |
| | 125 | 2 | 0 |
| 3 | 500 | 4 | 0 |
| | 250 | 4 | 0 |
| | 125 | 2 | 0 |
| 4 | 500 | 5 | 0 |
| | 250 | 4 | 0 |
| | 125 | 3 | 0 |
| | 500 | 4 | 0 |

Table 3-continued

| Test Compound No. | Amount of effective component (g/10a.) | Growth state of miscellaneous grasses | |
|---|---|---|---|
| | | large crab-grass | smooth pigweed |
| 5 | 250 | 4 | 0 |
| | 125 | 3 | 0 |
| 6 | 500 | 5 | 0 |
| | 250 | 4 | 0 |
| | 125 | 3 | 0 |
| 26 | 500 | 4 | 2 |
| | 250 | 3 | 0 |
| | 125 | 2 | 0 |
| 29 | 500 | 5 | 2 |
| | 250 | 5 | 1 |
| | 125 | 4 | 0 |
| 32 | 500 | 5 | 2 |
| | 250 | 4 | 1 |
| | 125 | 4 | 0 |
| 37 | 500 | 5 | 1 |
| | 250 | 4 | 0 |
| | 125 | 3 | 0 |
| 38 | 500 | 5 | 1 |
| | 250 | 4 | 0 |
| | 125 | 3 | 0 |
| 41 | 500 | 4 | 1 |
| | 250 | 4 | 0 |
| | 125 | 3 | 0 |
| 42 | 500 | 5 | 1 |
| | 250 | 4 | 0 |
| | 125 | 4 | 0 |
| 43 | 500 | 5 | 1 |
| | 250 | 4 | 0 |
| | 125 | 4 | 0 |
| 44 | 500 | 5 | 1 |
| | 250 | 4 | 0 |
| | 125 | 3 | 0 |
| 45 | 500 | 5 | 2 |
| | 250 | 4 | 0 |
| | 125 | 3 | 0 |
| 49 | 500 | 4 | 1 |
| | 250 | 4 | 0 |
| | 125 | 3 | 0 |
| The compound for the comparison | 500 | 3 | 0 |
| | 250 | 2 | 0 |
| | 125 | 1 | 0 |
| Untreated | — | 0 | 0 |

Test 3

Soil treating test

Soils was packed in a pot and about 15 grains of Barnyard grass seeds were sowed in it and a covering soils was softly laid upon them and the seeds were made to grow in a greenhouse, In the occasion that the seeds were germinated and the grass was grown to the first leaf stage, the said pot was put into a water stagnation conditions having 3 cm of water depth and each compound of wettable powder in accordance with Example 11 and was diluted with water to a specified concentration and the resulting each diluted aqueous suspension by a specified amount was respectively poured into each pot. In the course of 14th day after the above treatment, the growth of Barnyard grass was investigated. In compliance with the judgement standard for the growth state stipulated in Test 1, this investigating results were set forth in Table 4.

Table 4

| Test compound No. | Amount of effective component (g/10a.) | | |
|---|---|---|---|
| | 62.5 | 31.3 | 15.6 |
| 1 | 5 | 5 | 3 |
| 2 | 5 | 5 | 5 |
| 3 | 5 | 5 | 4 |
| 4 | 5 | 5 | 5 |
| 5 | 5 | 5 | 4 |
| 6 | 5 | 5 | 4 |
| 26 | 5 | 5 | 3 |
| 29 | 5 | 5 | 5 |
| 32 | 5 | 5 | 4 |
| 37 | 5 | 5 | 4 |
| 38 | 5 | 5 | 5 |
| 41 | 4 | 5 | 3 |
| 42 | 5 | 5 | 5 |
| 43 | 5 | 5 | 5 |
| 44 | 5 | 5 | 5 |
| 45 | 5 | 5 | 3 |
| 49 | 5 | 5 | 4 |
| The compound for the comparison | 3 | 1 | 0 |
| Untreated | 0 | 0 | 0 |

Test 4:

Test for selective effect

Soils was packed in a vat having 780 cm$^2$ of cross sectional area and seeds of barnyard grass, red bean, radish, cucumber, beet and tomato were sowed in the said soils of the pot and a covering soil was softly laid upon them and then, those seeds were germinated and grown in a greenhouse. In the occasion that those crops were grown to a height of 5 – 8 cm, the test compound of emulsifiable concentrate prepared with prescription of Example 13 was diluted to a specified concentration and the resulting diluted emulsified agent by 100 $l/10a$. of amount was sprayed over the stems and leaves of those crops. In the course of two weeks after above treating step, the growth state of those crops was investigated with naked eye judgement. In compliance with the judging standard for the growth state defined in Test 1, this investigating results were set forth in Table 5.

Table 5

| Test compound No. | Amount of effective component (g/10a.) | grass weeds barnyard grass | Broadleaf plant | | | | |
|---|---|---|---|---|---|---|---|
| | | | Beet | Cucumber | Radish | Red bean | Tomato |
| 1 | 150 | 5 | 0 | 0 | 0 | 0 | 0 |
| 2 | 150 | 5 | 0 | 0 | 0 | 0 | 0 |
| 3 | 150 | 5 | 0 | 0 | 0 | 0 | 0 |
| 4 | 150 | 5 | 1 | 0 | 0 | 0 | 0 |
| 5 | 150 | 5 | 0 | 0 | 0 | 0 | 0 |
| 6 | 150 | 4 | 0 | 0 | 0 | 0 | 0 |
| 26 | 150 | 4 | 0 | 0 | 0 | 0 | 0 |
| 29 | 150 | 5 | 1 | 0 | 0 | 0 | 0 |
| 32 | 150 | 5 | 0 | 0 | 0 | 1 | 0 |
| 37 | 150 | 5 | 0 | 0 | 0 | 0 | 0 |
| 38 | 150 | 5 | 0 | 0 | 0 | 0 | 0 |
| 41 | 150 | 4 | 0 | 0 | 0 | 0 | 0 |
| 42 | 150 | 5 | 0 | 0 | 0 | 0 | 0 |
| 43 | 150 | 5 | 0 | 0 | 0 | 1 | 0 |
| 44 | 150 | 5 | 0 | 0 | 0 | 0 | 0 |
| 45 | 150 | 5 | 0 | 0 | 0 | 0 | 1 |
| 49 | 150 | 4 | 0 | 0 | 0 | 0 | 0 |

Table 5-continued

| Test compound No. | Amount of effective component (g/10a.) | grass weeds barnyard grass | Beet | Broadleaf plant Cucumber | Radish | Red bean | Tomato |
| --- | --- | --- | --- | --- | --- | --- | --- |
| The compound for the comparison | 150 | 3 | 0 | 0 | 0 | 0 | 0 |
| Untreated plants | — | 0 | 0 | 0 | 0 | 0 | 0 |

Test 5:

Controlling test for inhibitting seed germination of weeds

Soils containing a mixture of large crab-grass seeds and common purslane seeds was packed in a pot having a surface area of 10 × 10 cm$^2$ and immediately, an emulsifiable concentrate of a test compound prepared in similar manner to Example 13 was diluted with water to a specified concentration and the resulting diluted emulsion was sprayed on the surface area of the soil and thereby a controlling treatment was carried out. In the course of the 21st day after the treating step, a growth state of weeds was investigated. A judging standard for the growth state was the same as test 1.

This investigating results are set forth in Table 6.

Table 6

| Test compound No. | Amount of effective component (g/10a.) | Growth state large crab-grass | common purslane |
| --- | --- | --- | --- |
| 60 | 500 | 5 | 5 |
|  | 250 | 4 | 3 |
|  | 125 | 3 | 2 |
| 63 | 500 | 5 | 5 |
|  | 250 | 5 | 4 |
|  | 125 | 4 | 2 |
| 64 | 500 | 5 | 5 |
|  | 250 | 5 | 3 |
|  | 125 | 3 | 1 |
| 65 | 500 | 5 | 5 |
|  | 250 | 5 | 4 |
|  | 125 | 3 | 0 |
| 66 | 500 | 5 | 5 |
|  | 250 | 4 | 2 |
|  | 125 | 3 | 1 |
| The compound for the comparison | 500 | 4 | 2 |
|  | 250 | 2 | 1 |
|  | 125 | 1 | 1 |

Test 6:

Test for foliar treatment

Soils was packed in a pot and seeds of barnyard grass and smooth pigweed were sowed in the said soils and a covering soils were softly laid upon them and those seeds were made to grow in a greenhouse. In occasion that the seeds were germinated and these seedlings were grown to a stage of sprouting the first leaf, an emulsifiable concentrate of a test compound prepared in similar manner to Example 13 was diluted with water to a specified concentration and the resulting diluted solution having the specified concentration by an amount of 100 l/10a. was respectively sprayed over stems and leaves of the plants and thus, the stem and leaf spraying treatment was carried out. In the course of 2 weeks after above treating step, growth state of the plants was investigated.

The results are shown in Table 7 with the values of 0 – 5 which have the same meaning of those of Test 1.

Table 7

| Test Compound No. | Amount of effective component (g/10A.) | Growth state barnyard grass | smooth pigweed |
| --- | --- | --- | --- |
| 61 | 500 | 5 | 5 |
|  | 250 | 5 | 5 |
|  | 125 | 4 | 2 |
| 62 | 500 | 5 | 5 |
|  | 250 | 5 | 5 |
|  | 125 | 4 | 4 |
| 63 | 500 | 5 | 5 |
|  | 250 | 5 | 5 |
|  | 125 | 5 | 5 |
| 65 | 500 | 5 | 5 |
|  | 250 | 5 | 5 |
|  | 125 | 4 | 3 |
| The compound for the comparison | 500 | 5 | 2 |
|  | 250 | 3 | 1 |
|  | 125 | 2 | 0 |

Test 7.

Test for soil treatment

Soils was packed in a pot and about 15 grains of barnyard grass seeds were sowed on the said soils and a covering soils was laid on the seeds and those seeds were made to grow in a greenhouse. In the occasion that the seeds were germinated and its seedlings were grown to a stage of sprouting the first leaf, the said pot was maintained in a water stagnation conditions with 3 cm of depth and an emulsifiable concentrate of each test compound prepared in similar manner to Example 13 was diluted to an each specified concentration and the resulting each diluted emulsion was resepctively poured into each spot. In the course of the 14th day and the 21st day after above treating step, the growth states of barnyard grass were respectively investigated. the results are shown in Table 8 with the values of 0 – 5 which have the same meaning of those of Test 1.

Table 8

| Test compound No. | Amount of effective component (g/10a.) | Growth state 14th day | 21st day |
| --- | --- | --- | --- |
| 60 | 200 | 5 | 5 |
|  | 100 | 5 | 5 |
|  | 50 | 5 | 5 |
| 61 | 200 | 5 | 5 |
|  | 100 | 5 | 5 |
|  | 50 | 4 | 5 |
| 63 | 200 | 5 | 5 |
|  | 100 | 5 | 5 |
|  | 50 | 5 | 5 |
| 64 | 200 | 5 | 5 |
|  | 100 | 5 | 5 |
|  | 50 | 5 | 5 |
| 65 | 200 | 5 | 5 |
|  | 100 | 5 | 5 |
|  | 50 | 5 | 5 |
| Compound | 200 | 5 | 5 |

Table 8-continued

| Test compound No. | Amount of effective component (g/10a.) | Growth state 14th day | 21st day |
|---|---|---|---|
| for the comparison | 100 | 4 | 4 |
| | 50 | 2 | 2 |

Test 8.

Test for selective herbicidal effect

Soils was packed in a vat having 780 cm² of superficial area and seeds of barnyard grass, red bean, radish, cucumber, beet, soy bean and tomato were sowed on the said soil and a covering soils was softly laid upon them and then, those seeds were made to grow in a greenhouse. In the occasion that those seeds were germinated and the seedings of those crops were grown to a height of 5 – 8 cm, an emulsifiable concentrate of a test compound prepared in similar manner to Example 13 was diluted with water to a specified concentration and the resulting diluted emulsion by 100 l/10a. of feed amount was respectively sprayed over stems and leaves of each crop. In the course of 10th day after above treating step, the growth states of those crops were investigated with judgement of naked eye. This investigating results in accordance with the judging standard of the growth state stigulated in test 1 are set forth in Table 9.

Table 9

| Compound No. for the experiment | Amount of effective component (g/10a.) | grass weeds barnyard grass | Plants of broad leaf crop red bean | radish | cucumber | beet | tomato | soybean |
|---|---|---|---|---|---|---|---|---|
| 60 | 150 | 4 | 0 | 3 | 3 | 4 | 5 | 0 |
| 62 | 150 | 4 | 0 | 3 | 4 | 3 | 5 | 0 |
| 64 | 150 | 5 | 0 | 4 | 3 | 5 | 4 | 0 |
| 65 | 150 | 5 | 0 | 4 | 4 | 4 | 2 | 0 |
| 66 | 150 | 5 | 0 | 4 | 3 | 4 | 4 | 0 |
| The compound for the comparison | 150 | 4 | 0 | 1 | 0 | 1 | 0 | 0 |

Test 9:

Test for growth control of Lawn

Lawns (species: Highland bent) at a growing stage in a spot having 9 cm of diameter was mowed with a small size of lawn mower so as its height may be about 1.5 cm of height.

In the course of the 2nd day after the mowing step, an emulsifiable concentrate of each compound prepared in similar manner to prescription of Example 13 was respectively diluted with water to a specified concentration and the resulting each diluted emulsion by 100 l/10a. of feed amount was sprayed over the mown lawns. In the course of the 5th day and the 12th day after the spraying step, a height of the lawns was respectively investigated This investigating results are set forth in Table 10. Above experiment was repeated 3 times.

Table 10

| Compound No. for the experiment | Amount of effective component (g/10a.) | Grass height (cm) 5th day after the treatment | 12th day after the treatment |
|---|---|---|---|
| 61 | 50 | 1.6 | 1.9 |
| | | 1.8 | 2.1 |
| | | 1.7 | 1.9 |

Table 10-continued

| Compound No. for the experiment | Amount of effective component (g/10a.) | Grass height (cm) 5th day after the treatment | 12th day after the treatment |
|---|---|---|---|
| 65 | 50 | 1.5 | 1.7 |
| | | 1.4 | 1.7 |
| | | 1.7 | 2.0 |
| | | 3.8 | 7.0 |
| Untreated zone | — | 3.5 | 7.5 |
| | | 3.8 | 7.0 |

Test 10.

Test for inhibitting seed germination and bud sprouting of weeds

A soils containing a mixture of large crab-grass seeds and common purslane seeds was packed in a put having 10 × 10 cm² of superficial area. Immediately, a wettable powder of test compound prepared in similar manner to Example 11 was diluted with water to a specified concentration and the resulting diluted aqueous suspension was sprayed over the soil surface. In the course of the 21st day after the spraying treatment, a growth state of weeds was investigated.

The results are shown in Table 11 with the values of 0 – 5 which have the same meanings as Test 1.

Table 11

| Test compound No. | Amount of effective component (g/10a.) | Growth state large crab-grass | common purslane |
|---|---|---|---|
| 69 | 250 | 5 | 1 |
| | 125 | 5 | 0 |
| | 62.5 | 4 | 0 |
| 72 | 250 | 5 | 2 |
| | 125 | 5 | 1 |
| | 62.5 | 4 | 0 |
| 74 | 250 | 5 | 2 |
| | 125 | 5 | 1 |
| | 62.5 | 5 | 0 |
| 75 | 250 | 5 | 2 |
| | 125 | 5 | 1 |
| | 62.5 | 5 | 0 |
| 76 | 250 | 5 | 1 |
| | 125 | 5 | 0 |
| | 62.5 | 4 | 0 |
| 78 | 250 | 5 | 2 |
| | 125 | 5 | 0 |
| | 62.5 | 5 | 0 |
| | 250 | 5 | 1 |
| The compound for the comparison | 125 | 3 | 1 |
| | 62.5 | 1 | 0 |

Test 11:

Test for treating the soils with water stagnation procedures

Soils was packed in a pot and about 15 grains of barnyard grass seeds were sowed on the said soils and a covering soils was softly laid upon them and those seeds were made to grow in a greenhouse. In the occasion that the germinated seedlings were grown at a stage of sprouting the first leaf, the said pot was maintained in a water stagnation conditions with 3 cm of water depth. Simultaneously, a wettable powder of each compound prepared in similar manner to Example 11 was diluted with water to a specified concentration and the resulting diluted aqueous suspension each compound by a definite amount was respectively poured into each pot. In the course of the 14th day after above treatment, the growth state of barnyard grass seedlings was investigated. The investigating results, in accordance with the judging standard for the growth state slipulated in Test 1 are set forth in Table 12.

Table 12

| Test compound No. | Amount of effective component (g/10a.) | | |
|---|---|---|---|
| | 125 | 62.5 | 31.5 |
| 67 | 5 | 5 | 4 |
| 68 | 5 | 5 | 4 |
| 70 | 5 | 5 | 4 |
| 71 | 5 | 5 | 4 |
| 73 | 5 | 5 | 5 |
| 74 | 5 | 5 | 4 |
| 75 | 5 | 5 | 5 |
| 77 | 5 | 5 | 5 |
| 79 | 5 | 5 | 5 |
| 82 | 5 | 5 | 5 |
| The compound for the comparison | 5 | 3 | 1 |

Test 12:

Test for foliar spraying treatment

A soils was packed in a pot and seeds of barnyard grass and smooth pigweed were sowed on the said soils and a covering soil was softly laid on it and those seeds were made to grow in a greenhouse. In the occasion that these seeds were germinated and the seedlings were grown at the stage of sprouting the first leaf, the wettable powder of each test compound prepared in similar manner to Example 11 was diluted with water to a specified concentration and the resulting diluted solution by 100 $l/10a$. of feed rate was sprayed and thereby the foliar spraying treatment was carried out. In the course of two weeks after the spraying treatment, the growth state of the plants was investigated. This investigating results, in accordance with the judging standard for the growth state stipulated in Test 1 are set forth in Table 13.

Table 13

| Test compound No. | Amount of effective component (g/10a.) | Growth state | |
|---|---|---|---|
| | | barnyard grass | smooth pigweed |
| 70 | 500 | 5 | 0 |
| | 250 | 4 | 0 |
| | 125 | 3 | 0 |
| 73 | 500 | 5 | 1 |
| | 250 | 4 | 0 |
| | 125 | 4 | 0 |
| 77 | 500 | 5 | 1 |
| | 250 | 5 | 0 |
| | 125 | 4 | 0 |
| 78 | 500 | 5 | 0 |
| | 250 | 4 | 0 |
| | 125 | 4 | 0 |
| 79 | 500 | 5 | 2 |
| | 250 | 5 | 0 |
| | 125 | 4 | 0 |
| 82 | 500 | 5 | 0 |
| | 250 | 5 | 0 |
| | 125 | 4 | 0 |
| The compound for the comparison | 500 | 3 | 0 |
| | 250 | 2 | 0 |
| | 125 | 1 | 0 |

Test 13:

Test for selective herbicidal effect

A soils was packed in a vat having 780 cm² of superficial area and those seeds of barnyard grass, red bean, radish, cucumber, beet and tomato were sowed on the said soils and a covering soils was softly laid upon them and those seeds were made to germinate are grown in a greenhouse. In the occasion that the seedlings of those crops were grown to a height of 5 to 8 cm, the wettable powder of each sampling compound prepared in similar manner to Example 11 was diluted with water to a specified concentration and the resulting diluted solution by 100 $l/10a$. of feed rate was respectively sprayed over of foliar each crop. In the course of the 10th day after the spraying treatment, the growth state for each crop was investigated with a judgement of naked eye. This investigating results, in accordance with the judgement standard for the growth state stipulated in Test 1 are set forth in Table 14.

Table 14

| Compound No. | Amount of effective component (g/10a.) | grass weeds | Broadleaf plants | | | | |
|---|---|---|---|---|---|---|---|
| | | barnyard grass | red bean | radish | cucumber | beet | tomato |
| 67 | 150 | 5 | 0 | 0 | 0 | 0 | 0 |
| 71 | 150 | 5 | 0 | 1 | 0 | 0 | 0 |
| 73 | 150 | 4 | 0 | 0 | 0 | 0 | 0 |
| 77 | 150 | 4 | 0 | 0 | 0 | 0 | 0 |
| 78 | 150 | 5 | 0 | 0 | 0 | 0 | 0 |
| 82 | 150 | 5 | 0 | 0 | 0 | 1 | 0 |
| The compound for the comparison | 150 | 3 | 0 | 0 | 0 | 0 | 1 |
| Untreated vat | — | 0 | 0 | 0 | 0 | 0 | 0 |

Test 14:

Test for controlling growth of yarn

A lawn (species : Highland bent) in the growing stage which was cultivated in a pot having 9 cm of diameter was mown to about 1.5 cm of height with a small size of lawn mower. In the course of the second day after above mowing operation, the wettable powder of each compound prepared in similar manner to Example 11 was diluted with water to a specified concentration and the resulting diluted solution by 100 l/10a. of feed rate was sprayed over the mown lawn. In the course of the 5th day and 12th day after above spraying step, both investigations for the heights of the lawn were carried out. This investigation results are set forth in Table 15.

Above test was repeated three times.

Table 15

| Compound No. | Amount of effective component for treatment (g/10a.) | Grass height after the 5th day (cm) | Grass height after the 12th day(cm) |
|---|---|---|---|
| 68 | 100 | 1.3 | 1.6 |
|  |  | 1.5 | 1.9 |
|  |  | 1.5 | 1.8 |
| 72 | 100 | 1.4 | 1.6 |
|  |  | 1.4 | 1.8 |
|  |  | 1.5 | 1.8 |
| 82 | 100 | 1.4 | 1.6 |
|  |  | 1.3 | 1.5 |
|  |  | 1.5 | 1.8 |
| Untreated | — | 3.8 | 7.0 |
|  |  | 3.5 | 7.5 |
|  |  | 3.8 | 7.0 |

Test 15.

Fungicidal test

Cucumber seeds (Kind : Sagami-Hampaku) were sowed and grown in a pot. In the stage of developing a cotyledon, wettable powder prepared in a similar manner to Example 11 was diluted to a specified concentration and the resulting diluted emulsion by 10 ml of amount was poured in the soil. On the next day after above pouring step, a fungus of Rhizoctonia solani which was cultured in a culture medium of wheat bran and chaff was inoculated on above cucumber seedling. In the course of 5th day after the inoculating step, the investigation was carried out and a preventive fungicidal value was calculated. This experiment was carried out for two pots in one testing section. Its average values are set forth in Table 6.

Table 16

| Sampling Compound No. | Preventive value |  |  |
|---|---|---|---|
|  | Concentration of effective component |  |  |
|  | 500 ppm | 250 ppm | 125 ppm |
| 4 | 100 | 100 | 86 |

Test 16.

Acaricidal test

Seeds of kidney beans were sowed in a pot and then, about 30 pieces of female adults to Tetranychus desertorum were inoculated on a main leaf of the kidney bean seedling in the course of 7 to 10 days after its sprouting stage. Then, on the next day, the injured insects were removed from it. An emulsifiable concentrate of each compound prepared in accordance with the prescription of Example 13 was diluted with water to a specified concentration and the resulting diluted chemical solution was sprayed over the said seeding. In the course of the 3rd day after the spraying step, its adjustment was carried out and adult mortality (%) was investigated.

This investigation was accorded with standard of the following evaluation grades as listed below.

| Adult mortality (%) | Evaluation grade |
|---|---|
| 100 | +++ |
| 80 to 99 | ++ |
| 5 to 79 | + |
| 0 to 49 | — |

Further, this investigation results by above evaluation grades are set forth in Table 7.

Table 7

| Test compound No. | Adult mortality |
|---|---|
| 4 | +++ |
| 41 | +++ |
| 44 | +++ |
| Untreated seedling of kidney bean | — |

What is claimed is:

1. A herbicidal composition comprising a herbicidally effective amount of a compound of the formula

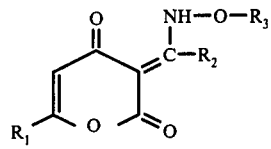

wherein $R_1$ is alkyl of 2 to 3 carbon atoms,
$R_2$ is alkyl of 2 to 3 carbon atoms and
$R_3$ is selected from the group consisting of ethyl and allyl.

2. A herbicidal composition comprising a herbicidally effective amount of a compound according to claim 1 in which $R_1$, $R_2$ and $R_3$ are ethyl group.

3. A herbicidal composition comprising a herbicidally effective amount of a compound according to claim 1 in which $R_1$ and $R_2$ are ethyl group and $R_3$ is allyl group.

4. A herbicidal composition comprising a herbicidally effective amount of a compound according to claim 1 in which $R_1$ is ethyl group, $R_2$ is propyl group and $R_3$ is ethyl group.

5. A herbicidal composition comprising a herbicidally effective amount of a compound according to claim 1 in which $R_1$ is ethyl group, $R_2$ is propyl group and $R_3$ is allyl group.

6. A herbicidal composition comprising a herbicidally effective amount of a compound according to claim 1 in which $R_1$ is propyl group, $R_2$ and $R_3$ are ethyl group.

7. A herbicidal composition comprising a herbicidally effective amount of a compound according to claim 1 in which $R_1$ is propyl group, $R_2$ is ethyl group and $R_3$ is allyl group.

8. A herbicidal composition comprising a herbicidally effective amount of a compound according to claim 1 in which $R_1$ and $R_2$ are propyl group and $R_3$ is ethyl group.

9. A herbicidal composition comprising a herbicidally effective amount of a compound according to claim 1 in which $R_1$ and $R_2$ are propyl group and $R_3$ is allyl group.

10. A method for the control of weeds comprising applying a compound of the formula

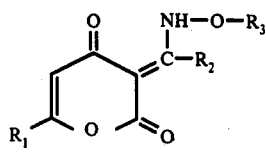

wherein $R_1$ is alkyl of 2 to 3 carbon atoms,
$R_2$ is alkyl of 2 to 3 carbon atoms and
$R_3$ is selected from the group consisting of ethyl and allyl,
in an amount sufficient to exert herbicidal action to a locus to be protected.

11. A method for the control of weeds comprising applying a compound according to claim 10 in which $R_1$, $R_2$ and $R_3$ are ethyl group in an amount sufficient to exert herbicidal action to a locus to be protected.

12. A method for the control of weeds comprising applying a compound according to claim 10 in which $R_1$ and $R_2$ are ethyl group and $R_3$ is allyl group in an amount sufficient to exert herbicidal action to a locus to be protected.

13. A method for the control of weeds comprising applying a compound according to claim 10 in which $R_1$ is ethyl group, $R_2$ is propyl group and $R_3$ is ethyl group in an amount sufficient to exert herbicidal action to a locus to be protected.

14. A method for the control of weeds comprising applying a compound according to claim 10 in which $R_1$ is ethyl group, $R_2$, is propyl group and $R_3$ is allyl group in an amount sufficient to exert herbicidal action to a locus to be protected.

15. A method for the control of weeds comprising applying a compound according to claim 10 in which $R_1$ is propyl group, $R_2$ and $R_3$ are ethyl group in an amount sufficient to exert herbicidal action to a locus to be protected.

16. A method for the control of weeds comprising applying a compound according to claim 10 in which $R_1$ is propyl group, $R_2$ is ethyl group and $R_3$ is allyl group in an amount sufficient to exert herbicidal action to a locus to be protected.

17. A method for the control of weeds comprising applying a compound according to claim 10 in which $R_1$ and $R_2$ are propyl group and $R_3$ is ethyl group in an amount sufficient to exert herbicidal action to a locus to be protected.

18. A method for the control of weeds comprising applying a compound according to claim 10 in which $R_1$ and $R_2$ are propyl group and $R_3$ is allyl group in an amount sufficient to exert herbicidal action to a locus to be protected.

* * * * *